US005788961A

United States Patent [19]
Marklund et al.

[11] Patent Number: 5,788,961
[45] Date of Patent: Aug. 4, 1998

[54] SUPEROXIDE DISMUTASE

[75] Inventors: Stefan Marklund; Thomas Edlund, both of Umea, Sweden

[73] Assignee: Symbicom Aktiebolag, Umela, Sweden

[21] Appl. No.: 446,104

[22] Filed: May 19, 1995

Related U.S. Application Data

[60] Continuation of Ser. No. 125,744, Sep. 24, 1993, Pat. No. 5,472,691, which is a division of Ser. No. 897,624, Jun. 12, 1992, Pat. No. 5,248,608, which is a continuation of Ser. No. 576,114, Aug. 27, 1990, Pat. No. 5,130,245, which is a continuation of Ser. No. 902,596, Sep. 2, 1986, abandoned.

[30] Foreign Application Priority Data

Sep. 3, 1985 [DK] Denmark ................................ 4027/85

[51] Int. Cl.$^6$ .................................................... A61K 38/44
[52] U.S. Cl. ................................................ 424/94.4; 435/189
[58] Field of Search ............................. 435/189; 424/94.4

[56] References Cited

U.S. PATENT DOCUMENTS

| 4,530,901 | 7/1985 | Weissmann | 435/76 |
|---|---|---|---|
| 4,738,927 | 4/1988 | Taniguchi et al. | 435/243 |

FOREIGN PATENT DOCUMENTS

| 8427461 | 1/1991 | Australia . |
| 19477 | of 0000 | European Pat. Off. . |
| 45222 | of 0000 | European Pat. Off. . |
| 0112299 | 6/1984 | European Pat. Off. . |
| 0138111 | 4/1985 | European Pat. Off. . |
| 0180964 | 5/1986 | European Pat. Off. . |
| 56-102787 | 8/1981 | Japan . |
| 57-155991 | 9/1982 | Japan . |
| 61-139390 | of 1986 | Japan . |

OTHER PUBLICATIONS

Marklund, CA 101:36464x; Mammalian Superoxide Dismutase (1984).
Fujisawa, CA 103:176901d; Superoxide Dismutase Production Using Monoclonal Antibodies (1985).
Affinity Chromotography, Principles and Methods (1979), Pharmaciz Fine Chemicals, pp. 92–93.
Southern, et al. in "Eukaryotic Viral Vectors", Cold Spring Harbor Lab (Y. Gluzman, ed.) (1982), pp. 41–45.
Suggs, et al., "Use of synthetic oligonucleotides as hybridization probes: Isolation of cloned cDNA sequences for human Beta2–microglubulin", Biochemistry 78:11:6613–6614, (Nov. 1981).
Marklund, S.L., "HUman copper–containing superoxide dismutase of high molecular weight", Proc. Natl. Acad. Sci. USA, 79:7634–7638, (Dec. 1982).
Kortt, et al., Eur. J. Biochem., 175: 141–49 (1988).
Zimmerman, Biol. Chem. Hoppe–Seyler, 369: 93–96 (Feb. 1988).
Chen, et al., Biochem. J., 203: 33–43 (1982).
Ozols, et al., The Journ. of Biological Chem., 244: 6617–6618 (Dec. 25, 1969).
Gibson, et al., The Journal of Biological Chem., 263: 4182–85 (Mar. 1988).
Fuchsman, Archives of Biochem. adn Biophysics, 243: 454–60 (Dec. 1985).
Mazrimas, et al., A Corrected Primary Sequence for Bull Protamine Biochimica et Biophysica Acta 872: 11–15 (1986).
Hu, et al., Cloning and Characterization of the Gene, Etc., Biochemistry 25: 7834–7839 (1986).
Panneerselvan, et al., Bovine Parathymosin: Amino Acid Sequence, Etc., Biochem & Biophys. Res. Comm., 155: 539–545 (Sep. 1988).
Mitchel, et al., The Complete Amino Acid, Etc., The Journal of Biological Chem., 245: 3485–3492 (1970).
Knecht, et al., Sequence Determination of Eglin, Etc., Analytical Biochemistry, 130: 65–71 (1983).
Fridovich, (1974) Adv. Enz. Rel Areas, p. 64.
R. Lathe, Synthetic Oligonucleotide Probes, ETc., J. Mol. Biol. 183: 1–12 (1985).
Schneider, et al., Procedure for Production of Hybrid, Etc., Proc. Natl. Aca. Sci. 78: 2169–2173 (1981).
Wang, et al., Site–Specific Mutagenesis, Etc., 1431–1433 (Jun. 1984).
Fersht, et al., Fine Structure–Activity Analysis, Etc., Bio–Chemistry, 24: 5858–5861 (1985).
Carter, et al., The Use of Double Mutants, Etc., Cell., 38: 835–40 (Oct. 1984).
Parge, et al., Crystallographic Chracterization, ETc., The Journal of Biol. Chem., 261: 16215–18 (1986).
Beyer, et al., Examination of the Role of Arginine, Etc., 262: 11182–87 (1987).
Creighton, Structure and Molecular Princ., Proteins, 37–42, 45–47, 110–112, 128, 129, 235, 259, 352–366 (1983).
Schulz, et al., Principles of Protein Structure, 2, 3, 10–12, 14–16, 168–174 (1979).
Shively, et al., Anal. Biochem., 120: 312–322 (1982).
Marklund, Holme and Hellner, Clinica Chimica Acta 126:41–51 (1982).
Marklund, Biochem. J., 220:269–72 (1984).
Marklund, J. Clin. Invest., 74:1398–1403 (1984).
Marklund, Biochem J., 222:649–55 (1984).
Duplay et al., "Linker Mutagenesis in the GeneEncoding The Periplasmic Maltose–Binding Protein of E.Coli.", Biochimie, 1985, 67, 849–851.

(List continued on next page.)

*Primary Examiner*—Charles L. Patterson, Jr.
*Attorney, Agent, or Firm*—Iver P. Cooper

[57] ABSTRACT

A superoxide dismutase originally found in extracellular body fluids and therefore termed extracellular superoxide dismutase (EC-SOD) is prepared by growing a cell line, preferably of mammalian origin, producing EC-SOD and recovering the EC-SOD secreted from the cells or by inserting a DNA sequence encoding EC-SOD into a suitable vector, introducing the recombinant vector into a host cell, growing the cell and recovering the EC-SOD produced.

EC-SOD may be used for the prophylaxis or treatment of diseases or disorders associated with the presence or formation of superoxide radicals.

9 Claims, 16 Drawing Sheets

OTHER PUBLICATIONS

Wells, et al., "Cassette Mutagenesis: An Efficient Method for Generation of Multiple Mutations at Defined Sites", Gene, 34 (1985) 315–323.

Milton et al., "In Vitro Mutagenesis and Overexpression of the *Escherichia Coli* trpA Gene and the Partial Characterization of the Resultant Tryptophan Synthase Mutant Alpha–Subunits", J. Bio. Chem., 261 (1986) 16604–16615.

Matteucci et al., "Integrated Random Mutagenesis: The Use of Ambiguously Synthesized Oligonucleotides to Mutagenize Sequences Immediately 5' of an ATG Initiation Codon", Nuc. Acids. Res., vol. 11, No. 10, 1983, 3113–3121.

Myers, et al., "General Method for Saturation Mutagenesis of Cloned DNA Fragments", Science, vol. 229, 242–247 (1985).

Abarzua et al., "Enzymatic Techniques for the Isolation of Random Single–Base Substitutions in vitro at High Frequency", Proc. Natl. Acad. Sci. USA, 81, 2030–2034, Apr. 1984.

Hjalmarssson et al., "Isolation and Sequence of Complementary DNA Encoding Human Extracellular Superoxide Dismutase", Proc. Natl. Acad. Sci. USA, 84: 6340–6344, Sep. 1987.

Adachi et al., "Interactions Between Human Extracellular Superoxide Dismutase C and Sulfated Polysaccharides", J. Bio. Chem., 264:8537–8541, 1989, No. 15.

Borders et al., "Identification of ARG–143 As the Essential Arginyl Residue in Yeast Cu, Zn Superoxide Dismutase by Use of a Chromophoric Arginine Reagent", Bio. and Biop. Res. Comm., 96:1071–1078, No. 3, 1980.

Malinowski et al., "Chemical Modification of Arginine at the Active Site of the Bovine Erythrocyte Superoxide Dismutase", Biochemistry, 18:5909–5917, No. 26, 1979.

Steffens, et al., "The Primary Structure of Cu–Zn Superoxide Dismutase from Photobacterium Biognathi: Evidence for a Separate Evolution of CuZn Superoxide Dismutase in Bacteria", Hoppe–Seylers Z. Phy. Chem. 364:675–90(1983).

Bannister et al., "The Presence of a Copper/Zinc Superoxide Dismutase in the Bacterium Photobacterium Leiognathi: A Likely Case of Gene Transfer From Eukaryotes to Prokaryotes", Proc. Nat. Acad. Sci., 82:149–152, Jan. 1985.

Rocha, et al., "The Amino Acid Sequence of Copper/Zinc Superoxide Dismutase from Swordfish Liver –Comparison f Copper/Zinc Superoxide Dismutase Sequences", Eur. J. Biochem., 145:477–484 (1984).

Lee et al., "Superoxide Dismutase: An Evolutionary Puzzle", Proc. Natl. Acad. Sci. USA, 82:824–828, 1985.

Steinman, "The Amino Acid Sequence of Copper–Zinc Superoxide Dismutase from Bakers' Yeast", J. Biol. Chem., 255, No. 14, 6758–6765 (1980).

Kitagawa, et al., "Amino Acid Sequence of Copper, Zinc–Superoxide Dismutase from Spinach Leaves", J. Biochem., 99:1289–1298 (1986), vol. 99, No. 5.

Hering et al., "The Primary Structure of Procine Cu–Zn Superoxide Dismutase Evidence for Allotypes of Superoxide Dismutase in Pigs", Bio. Chem. Hoppe–Seyler, 366:435–445 (Apr. 1985).

Lerch, et al., "Amino Acid Sequence of Copper–Zinc Superoxide Dismutase from Horse Liver", J. Bio. Chem., 256, No. 22, 11545–11551 (1981).

Steinman, et al., "Bovine Erythrocyte Superoxide Dismutase", J. Biol. Chem. 249, No. 22, 7326–7338 (1974).

Sherman, et al., "Nucleotide Sequence and Expression of Human Chromosome 21–encoded Superoxide Dismutase mRNA", Proc. Natl. Acad. Sci., USA, 80: 5465–5469 (Sep. 1983).

Hallewell, et al., "Human Cu/Zn Superoxide Dismutase cDNA:Isolation of Clones Synthesizing High Levels of Active or Inactive Enzyme from an Expression Library", 13, No. 6, 2017–2034 (1985).

Tainer, et al., "Determination and Analysis of the 2 A Structure of Copper, Zinc Superoxide Dismutase", J. Mol. Biol. (1982) 160, 181–217.

Bermingham–McDonogh et al., "Reduced Anion–Binding Affinity of Cu, Zn Superoxide Dismutases Chemically Modified at Arginine", 108:1376–1382 No. 4 (1982), Biochem. Biophys. Res. Commun.

Borders, Jr. et al., "Essential Arginyl Residues in Cu,Zn Superoxide Dismutase from *Saccharomyces Cerevisiae*", Carbohydr. Res. Commun., vol. 45, 185–194 (1980).

Getzoff et al., "Electrostatic Recognition Between Superoxide and Copper, Zinc Superoxide Dismutase", Nature, 306:287–290 (Nov. 1983).

Tainer et al., "Structure and Mechanism of Copper, Zinc Superoxide Dismutase", Nature, 306:284–286 (Nov. 1983).

Amuro, et al. "Replacement by Site–directed Mutagenesis Indicates a Role for Histidine 170 in the Glutamine Amide Transfer Function of Anthranilate Synthase", J. Biol. Chem., 260:14844–14849, No. 27 (1985).

Borders, et al., "Essentiality of the Active–Site Arginine Residue for the Normal Catalytic Activity of Cu, Zn Superoxide Dismutase", Biochem., J. 230:771–776 (1985).

McLachlan, "Tests for Comparing Related Amino–Acid Sequences, Cytochrome C and Cytochrome C551", J. Mol. Biol., 61:409–424 (1971).

Botstein, et al., "Strategies and Applications of In Vitro Mutagenesis", 229:1193–1201, Science, (Sep. 20, 1985), No. 4719.

Fasano, et al., "Analysis of the Transforming Potential of the Human H–ras Gene by Random Mutagenesis", Proc. Natl. Acad. Sci. USA, 81:4008–4012 (Jul. 1984).

Suzuki et al. "Domain Structure of Vitronectin", J. Biochem., 259:15307–15314, No. 24, 1984.

Calaycay et al. "Primary Structure of a DNA–and Heparin–binding Domain (Domain III) in Human Plasma Fibronectin", J. Biochem., 260:12136–12141, (1985).

Busch, C, et. al. (1980) Throm. Res. 19, 129–137.

Robinson–White, A, et al. (1985) J. Clin. Invest. 76, 93–100.

```
CTGGGTGCAGCTCTCTTTTCAGGAGAGAAAGCTCTCTTGGAGGAGCTGGAAAGGTGCCCG
GACCCACGTCGAGAGAAAAGTCCTCTCTTTCGAGAGAACCTCCTCGACCTTTCCACGGGC
1                                                          60
       -18                       -10
         MetLeuAlaLeuLeuCysSerCysLeuLeuLeuAlaAlaGlyAlaSerAsp
ACTCCAGCCATGCTGGCGCTACTGTGTTCCTGCCTGCTCCTGGCAGCCGGTGCCTCGGAC
TGAGGTCGGTACGACCGCGATGACACAAGGACGGACGAGGACCGTCGGCCACGGAGCCTG
                                                          120

-1 +1                         10
AlaTrpThrGlyGluAspSerAlaGluProAsnSerAspSerAlaGluTrpIleArgAsp
GCCTGGACGGGCGAGGACTCGGCGGAGCCCAACTCTGACTCGGCGGAGTGGATCCGAGAC
CGGACCTGCCCGCTCCTGAGCCGCCTCGGGTTGAGACTGAGCCGCCTCACCTAGGCTCTG
                                                          180

20                         30
MetTyrAlaLysValThrGluIleTrpGlnGluValMetGlnArgArgAspAspAspGly
ATGTACGCCAAGGTCACGGAGATCTGGCAGGAGGTCATGCAGCGGCGGGACGACGACGGC
TACATGCGGTTCCAGTGCCTCTAGACCGTCCTCCAGTACGTCGCCGCCCTGCTGCTGCCG
                                                          240

40                         50
ThrLeuHisAlaAlaCysGlnValGlnProSerAlaThrLeuAspAlaAlaGlnProArg
ACGCTCCACGCCGCCTGCCAGGTGCAGCCGTCGGCCACGCTGGACGCCGCGCAGCCCCGG
TGCGAGGTGCGGCGGACGGTCCACGTCGGCAGCCGGTGCGACCTGCGGCGCGTCGGGGCC
                                                          300

60                         70
ValThrGlyValValLeuPheArgGlnLeuAlaProArgAlaLysLeuAspAlaPhePhe
GTGACCGGCGTCGTCCTCTTCCGGCAGCTTGCGCCCCGCGCCAAGCTCGACGCCTTCTTC
CACTGGCCGCAGCAGGAGAAGGCCGTCGAACGCGGGGCGCGGTTCGAGCTGCGGAAGAAG
                                                          360

80                         90
AlaLeuGluGlyPheProThrGluProAsnSerSerSerArgAlaIleHisValHisGln
GCCCTGGAGGGCTTCCCGACCGAGCCGAACAGCTCCAGCCGCGCCATCCACGTGCACCAG
CGGGACCTCCCGAAGGGCTGGCTCGGCTTGTCGAGGTCGGCGCGGTAGGTGCACGTGGTC
                                                          420

100                        110
PheGlyAspLeuSerGlnGlyCysGluSerThrGlyProHisTyrAsnProLeuAlaVal
TTCGGGGACCTGAGCCAGGGCTGCGAGTCCACCGGGCCCCACTACAACCCGCTGGCCGTG
AAGCCCCTGGACTCGGTCCCGACGCTCAGGTGGCCCGGGGTGATGTTGGGCGACCGGCAC
                                                          480

120                        130
ProHisProGlnHisProGlyAspPheGlyAsnPheAlaValArgAspGlySerLeuTrp
CCGCACCCGCAGCACCCGGGCGACTTCGGCAACTTCGCGGTCCGCGACGGCAGCCTCTGG
GGCGTGGGCGTCGTGGGCCCGCTGAAGCCGTTGAAGCGCCAGGCGCTGCCGTCGGAGACC
                                                          540

140                        150
ArgTyrArgAlaGlyLeuAlaAlaSerLeuAlaGlyProHisSerIleValGlyArgAla
AGGTACCGCGCCGGCCTGGCCGCCTCGCTCGCGGGCCCGCACTCCATCGTGGGCCGGGCC
TCCATGGCGCGGCCGGACCGGCGGAGCGAGCGCCCGGGCGTGAGGTAGCACCCGGCCCGG
                                                          600
```

FIG. 5A

```
                160                              170
ValValValHisAlaGlyGluAspAspLeuGlyArgGlyGlyAsnGlnAlaSerValGlu
GTGGTCGTCCACGCTGGCGAGGACGACCTGGGCCGCGGCGGCAACCAGGCCAGCGTGGAG
CACCAGCAGGTGCGACCGCTCCTGCTGGACCCGGCGCCGCCGTTGGTCCGGTCGCACCTC
                                                          660
                180                              190
AsnGlyAsnAlaGlyArgArgLeuAlaCysCysValValGlyValCysGlyProGlyLeu
AACGGGAACGCGGGCCGGCGGCTGGCCTGCTGCGTGGTGGGCGTGTGCGGGCCCGGGCTC
TTGCCCTTGCGCCCGGCCGCCGACCGGACGACGCACCACCCGCACACGCCCGGGCCCGAG
                                                          720
                200                              210
TrpGluArgGlnAlaArgGluHisSerGluArgLysLysArgArgArgGluSerGluCys
TGGGAGCGCCAGGCGCGGGAGCACTCAGAGCGCAAGAAGCGGCGGCGCGAGAGCGAGTGC
ACCCTCGCGGTCCGCGCCCTCGTGAGTCTCGCGTTCTTCGCCGCCGCGCTCTCGCTCACG
                                                          780
                220
LysAlaAla***
AAGGCCGCCTGAGCGCGGCCCCCACCCGGCGGCGGCCAGGGACCCCCGAGGCCCCCCTCT
TTCCGGCGGACTCGCGCCGGGGTGGGCCGCCGCCGGTCCCTGGGGGCTCCGGGGGGAGA
                                                          840
GCCTTTGAGCTTCTCCTCTGCTCCAACAGACACCTTCCACTCTGAGGTCTCACCTTCGCC
CGGAAACTCGAAGAGGAGACGAGGTTGTCTGTGGAAGGTGAGACTCCAGAGTGGAAGCGG
                                                          900
TCTGCTGAAGTCTCCCCGCAGCCCTCTCCACCCAGAGGTCTCCCTATACCGAGACCCACC
AGACGACTTCAGAGGGGCGTCGGGAGAGGTGGGTCTCCAGAGGGATATGGCTCTGGGTGG
                                                          960
ATCCTTCCATCCTGAGGACCGCCCCAACCCTCGGAGCCCCCCACTCAGTAGGTCTGAAGG
TAGGAAGGTAGGACTCCTGGCGGGGTTGGGAGCCTCGGGGGTGAGTCATCCAGACTTCC
                                                         1020
CCTCCATTTGTACCGAAACACCCCGCTCACGCTGACAGCCTCCTAGGCTCCCTGAGGTAC
GGAGGTAAACATGGCTTTGTGGGCGAGTGCGACTGTCGGAGGATCCGAGGGACTCCATG
                                                         1080
CTTTCCACCCAGACCCTCCTTCCCCACCCCATAAGCCCTGAGACTCCCGCCTTTGACCTG
GAAAGGTGGGTCTGGGAGGAAGGGGTGGGGTATTCGGGACTCTGAGGGCGGAAACTGGAC
                                                         1140
ACGATCTTCCCCCTTCCCGCCTTCAGGTTCCTCCTAGGCGCTCAGAGGCCGCTCTGGGGG
TGCTAGAAGGGGGAAGGGCGGAAGTCCAAGGAGGATCCGCGAGTCTCCGGCGAGACCCC
                                                         1200
GTTGCCTCGAGTCCCCCCACCCCTCCCCACCCACCACCGCTCCCGCGGCAAGCCAGCCCG
CAACGGAGCTCAGGGGGTGGGGAGGGTGGGTGGTGGCGAGGGCGCCGTTCGGTCGGC
                                                         1260
TGCAACGGAAGCCAGGCCAACTGCCCCGCGTCTTCAGCTGTTTCGCATCCACCGCCACCC
ACGTTGCCTTCGGTCCGGTTGACGGGGCGCAGAAGTCGACAAAGCGTAGGTGGCGGTGGG
                                                         1320
CACTGAGAGCTGCTCCTTTGGGGAATGTTTGGCAACCTTTGTGTTACAGATTAAAAATT
GTGACTCTCGACGAGGAAACCCCCTTACAAACCGTTGGAAACACAATGTCTAATTTTTAA
                                                         1380
CAGCAATTCAAAAAAA
GTCGTTAAGTTTTTTT
       1396
```

FIG. 5B

SUPEROXIDE DISMUTASE

This is a continuation of application Ser. No. 08/125,744 filed Sep. 24, 1993, now U.S. Pat. No. 5,472,691, which is a division of application Ser. No. 07/897,624 filed Jun. 12, 1992, now U.S. Pat. No. 5,248,608, which is a continuation of application Ser. No. 07/576,114, now U.S. Pat. No. 5,130,245 filed Aug. 27, 1990, which is a continuation of application Ser. No. 06/902,596 filed Sep. 2, 1986, now abandoned, the contents of all of which are hereby incorporated by reference.

The present invention relates to a superoxide dismutase, methods of producing the superoxide dismutase and the use thereof for the purpose of therapeutic treatment.

There is a very strong thermodynamic driving force for the reactions between oxygen and biochemical compounds in the body such as proteins, carbohydrates, lipids and nucleic acids. If such reactions go to completion, water, carbon dioxide and a number of waste products are formed as end products concomitantly with the release of large amounts of energy. Oxidation of biological compounds is the source of energy of living organisms. Fortunately such reactions occur spontaneously very slowly due to reaction barriers. These barriers are overcome by the enzymes in intermediary metabolism, and the final reaction with oxygen takes place in the mitochondria, where the oxygen is reduced by four electrons to water without the liberation of any intermediate products. The reaction is accomplished by cytochrome oxidase complex in the electron transport chain and the energy is bound by the formation of ATP.

However, the direct four-step reduction of oxygen to water is almost unique, and when oxygen reacts spontaneously or catalysed by enzymes it is forced to react one step at a time for mechanistic reasons (enzyme-catalysed reactions sometimes require two steps). A series of reactive and toxic intermediates are formed, namely the superoxide radical ($O_2^{-}$), hydrogen peroxide ($H_2O_2$), and the hydroxyl radical (OH·) in that order, as shown below:

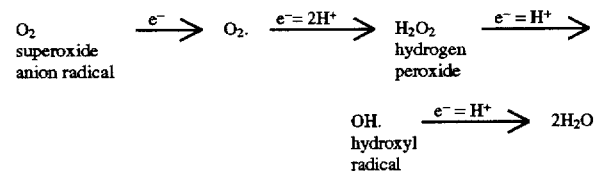

Two these, $O_2^{-}$ and OH·, have single unpaired electrons and are therefore called free radicals. A few percent of the oxygen consumption in the body has been estimated to lead to the formation of the toxic reduction intermediates. The toxic effects of oxygen are mainly ascribable to the actions of these intermediates.

Oxygen in itself reacts slowly with most biochemical compounds. The toxic reactions are in general initiated by processes giving rise to oxygen radicals, which in themselves cause direct damage to biochemical compounds or start chain reactions involving oxygen.

Some compounds react spontaneously with oxygen, i.e. they autoxidize. Virtually all autoxidations result in the formation of toxic oxygen reduction intermediates. Autoxidation of adrenalin, pyrogallol and several other compounds leads to the formation of the superoxide radical. The superoxide radical is also released when methemoglobin is formed from oxyhemoglobin. Furthermore, some oxidases form superoxide. The most important of these enzymes is xanthine oxidase, which oxidizes hypoxanthine and xanthine to uric acid. A minor part of the oxygen reduction in mitochondria leads to the formation of superoxide and subsequently hydrogen peroxide. The microsomal cytochrome $P_{450}$ system also releases superoxide. When ionizing radiation passes through an aqueous solution containing oxygen, the superoxide radical is the radical formed in the highest concentration. Upon activation of phagocytosing leukocytes (polymorphonuclears, monocytes, macrophages, eosinophils) large amounts of superoxide are released. The toxic oxygen reduction products so formed are of fundamental importance for the killing ability of the cells, but might also lead to damage in the surrounding tissue.

Hydrogen peroxide is always formed when superoxide is formed by way of the dismutation reaction. Most oxidases in the body directly reduce oxygen to hydrogen peroxide.

The most reactive of the intermediates is the hydroxyl radical. It can be formed when hydrogen peroxide reacts with $Fe^{2+}$ or $Cu^{+}$ ions, the so-called Fenton reaction.

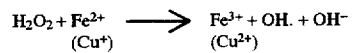

These transition metal ions may also catalyze a reaction between hydrogen peroxide and superoxide leading to hydroxyl radical production, the so-called Haber-Weiss reaction.

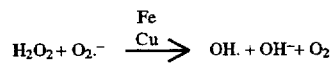

Ionizing radiation cleaves water with formation of hydrogen atoms and hydroxyl radicals. The hydroxyl radicals so formed account for most of the biological damage caused by ionizing radiation.

It appears from the above description that several of the oxygen reduction products are normally formed at the same time. In the xanthine oxidase system, for example, not only is superoxide formed, but also hydrogen peroxide, both directly and by superoxide dismutation. These compounds may then react further to form the hydroxyl radical. The xanthine oxidase system can be demonstrated to damage proteins, carbohydrates and nucleic acids and to kill cells. Of the biochemical compounds, polyunsaturated lipids appear to be the most sensitive to oxygen toxicity. The oxygen intermediates can initiate chain reactions involving molecular oxygen, the so-called lipid peroxidation. The lipid hydroperoxides so formed and their degradation products not only impair the function of the cell membranes, but may also damage other cell components.

Organisms living in the presence of oxygen have been forced to develop a number of protective mechanisms against the toxic oxygen reduction metabolites. The protective factors include superoxide dismutases (SOD) which dismutate the superoxide radical and are found in relatively constant amounts in mammalian cells and tissue. The best known of these enzymes is CuZn SOD which is a dimer with a molecular weight of 33,000 containing two copper and two zinc atoms. CuZn SOD is found in the cytosol and in the intermembrane space of the mitochondria. Mn SOD is a tetramer with a molecular weight of 85,000 containing 4 Mn atoms, and is mainly located in the mitochondrial matrix. Until recently, the extracellular fluids were assumed to lack SOD-activity.

However, the present inventors have recently demonstrated the presence of a superoxide dismutase in extracellular fluids (e.g. blood plasma, lymph, synovial fluid and cerebrospinal fluid) which was termed EC-SOD (extracellular superoxide dismutase). In humans, the activity per ml of plasma is less than 1% of the total SOD-activity per g of tissue, but it seems to be actively regulated by the body (Marklund et al., *Clin. Chim. Acta* 126, 1982, pp. 41–51). The affinity for lectins (cf. Example 12) indicates that, contrary to CuZn SOD, the enzyme is a glycoprotein. It seems to be composed of four equal non-covalently bound subunits with a total (tetramer) molecular weight of 135,000, and with a metal content of one Cu atom and one Zn atom per subunit (cf. Example 14). The enzyme catalyzes a first-order dismutation of the superoxide radical, as do other Cu-containing SODs.

$$O_2^{-} + O_2^{-} + 2H^{+} \xrightarrow{SOD} O_2 + H_2O_2$$

The specific activity is very high and is probably mediated by the four Cu atoms of the molecule. Upon chromatography on heparin-Sepharose®, the enzyme is divided into three fractions, A without any affinity, B with a weak affinity and C with a strong heparin affinity. Unlike the behaviour of EC-SOD, CuZn SOD and Mn SOD do not bind to heparin-Sepharose®. The enzyme has a certain hydrophobic character which may indicate an affinity for cell membranes. Affinity for heparin often indicates affinity for heparan sulfate which is found on cell surfaces, especially on vessel endothelium. It may therefore be assumed that EC-SOD is partly localized on cell surfaces and partly in extracellular fluids (cf. Example 9–11 below). The amino acid composition and the antigenic reactivity is quite unlike that of the hitherto investigated SOD isoenzymes (Marklund, *Proc. Nat. Acad. Sci. USA* 79, 1982, pp. 7634–7638; *Biochem. J.* 220, 1984, pp. 269–272). The messenger RNA encoding EC-SOD comprises a sequence coding for a signal peptide (cf. Example 8), indicating that EC-SOD is a secreted protein. The mRNA coding for CuZn SOD, on the other hand, does not comprise such a sequence coding for a signal peptide. Furthermore, the amino acid sequence of EC-SOD is different from that of the other SOD isoenzymes; EC-SOD has been shown to be present in the plasma of all the mammalian species examined (Marklund, *J. Clin. Invest.* 74, 1984, pp. 1398–1403; *Biochem. J.* 222, 1984, pp. 649–655) as well as in birds and fish. The content varies widely between the species, but intraspecies variation is very small. Rodent plasma contains 10–20 times more EC-SOD than human plasma which contains comparatively little EC-SOD. EC-SOD has also been found in all the different types of animal tissue examined (Marklund, *J. Clin. Invest.* 74, 1984, pp. 1398–1403; *Biochem. J.* 222, 1984, pp. 649–655). In tissues the interspecies differences are far smaller. The level of EC-SOD in tissues (units per gram of wet weight) is higher than the level of plasma EC-SOD (units/ml) in humans. In rodents, the tissue and plasma contain approximately equal amounts of EC-SOD (Marklund, *Biochem. J.* 222, 1984, pp. 649–655).

The activity of the SODs make them interesting candidates for therapeutic agents to counteract the toxic effects of the superoxide and other oxygen radicals.

Because of the above-mentioned low level of SOD activity in extracellular fluids, the components in the extracellular fluids and the cell surfaces are far less protected against superoxide radicals and the other toxic oxygen reduction products than the cell interior. EC-SOD therefore constitutes a particularly interesting substance for therapeutic applications in connection with extracellular superoxide radical production.

It would therefore be advantageous to provide EC-SOD in realistic quantities for therapeutic purposes from an easily available source. Such sources which primarily comprise specific types of cells have not previously been suggested or described.

Hence, in an important aspect, the present invention relates to EC-SOD of recombinant origin. In the present context, the term "recombinant" is intended to indicate that the EC-SOD is derived from a cell which has been subjected to recombinant DNA techniques, i.e. into which a DNA sequence coding for EC-SOD has been inserted and which has subsequently been induced to express EC-SOD. More particularly, the invention relates to EC-SOD which has a polypeptide structure encoded by the following DNA sequence

```
Trp Thr Gly Glu Asp Ser Ala Glu Pro Asn Ser Asp Ser Ala Glu Trp Ile Arg Asp Met
TGGACGGGCGAGGACTCGGCGGAGCCCAACTCTGACTCGGCGGAGTGGATCCGAGACATG
ACCTGCCCGCTCCTGAGCCGCCTCGGGTTGAGACTGAGCCGCCTCACCTAGGCTCTGTAC 30                              40
Tyr Ala Lys Val Thr Gly Ile Trp Gln Glu Val Met Gln Arg Arg Asp Asp Asp Gly Thr
TACGCCAAGGTCACGGAGATCTGGCAGGAGGTCATGCAGCGGCGGGACGACGACGGCACG
ATGCGGTTCCAGTGCCTCTAGACCGTCCTCCAGTACGTCGCCGCCCTGCTGCTGCCGTGC 50                              60
Leu His Ala Ala Cys Gln Val Gln Pro Ser Ala Thr Leu Asp Ala Ala Gln Pro Arg Val
CTCCACGCCGCCTGCCAGGTGCAGCCGTCGGCCACGCTGGACGCCGCGAGCCCCGGGTG
GAGGTGCGGCGGACGGTCCACGTCGGCAGCCGGTGCGACCTGCGGCGCGTCGGGGCCCAC 70                              80
Thr Gly Val Val Leu Phe Arg Gln Leu Ala Pro Arg Ala Lys Leu Asp Ala Phe Phe Ala
ACCGGCGTCGTCCTCTTCCGGCAGCTTGCGCCCCGCGCCAAGCTCGACGCCTTCTTCGCC
TGGCCGCAGCAGGAGAAGGCCGTCGAACGCGGGGCGCGGTTCGAGCTGCGGAAGAAGCGG 90                              100
Leu Glu Gly Phe Pro Thr Glu Pro Asn Ser Ser Ser Arg Ala Ile His Val His Gln Phe
CTGGAGGGCTTCCCGACCGAGCCGAACAGCTCCAGCCGCGCCATCCACGTGCACCAGTTC
GACCTCCCGAAGGGCTGGCTCGGCTTGTCGAGGTCGGCGCGGTAGGTGCACGTGGTCAAG 110                             120
Gly Asp Leu Ser Gln Gly Cys Glu Ser Thr Gly Pro His Tyr Asn Pro Leu Ala Val Pro
GGGGACCTGAGCCAGGGCTGCGAGTCCACCGGGCCCCACTACAACCCGCTGGCCGTGCCG
CCCCTGGACTCGGTCCCGACGCTCAGGTGGCCCGGGGTGATGTTGGGCGACCGGCACGGC
```

-continued

```
                      130                                                140
His Pro Gln His Pro Gly Asp Phe Gly Asn Phe Ala Val Arg Asp Gly Ser Leu Trp Arg
CACCCGCAGCACCCGGGCGACTTCGGCAACTTCGCGGTCCGCGACGGCAGCCTCTGGAGG
GTGGGCGTCGTGGGCCCGCTGAAGCCGTTGAAGCGCCAGGCGCTGCCGTCGGAGACCTCC 150                                                160
Tyr Arg Ala Gly Leu Ala Ala Ser Leu Ala Gly Pro His Ser Ile Val Gly Arg Ala Val
TACCGCGCCGGCCTGGCCGCCTCGCTCGCGGGCCCGCACTCCATCGTGGGCCGGGCCGTG
ATGGCGCGGCCGGACCGGCGGAGCGAGCGCCCGGGCGTGAGGTAGCACCCGGCCCGGCAC 170                                                180
Val Val His Ala Gly Glu Asp Asp Leu Gly Arg Gly Gly Asn Gln Ala Ser Val Glu Asn
GTCGTCCACGCTGGCGAGGACGACCTGGGCCGCGGCGGCAACCAGGCCAGCGTGGAGAAC
CAGCAGGTGCGACCGCTCCTGCTGGACCCGGCGCCGCCGTTGGTCCGGTCGCACCTCTTG 190                                                200
Gly Asn Ala Gly Arg Arg Leu Ala Cys Cys Val Val Gly Val Cys Gly Pro Gly Leu Trp
GGGAACGCGGGCCGGCGGCTGGCCTGCTGCGTGGTGGGCGTGTGCGGGCCCGGGCTCTGG
CCCTTGCGCCCGGCCGCCGACCGGACGACGCACCACCCGCACACGCCCGGGCCCGAGACC 210                                                220
Glu Arg Gln Ala Arg Glu His Ser Glu Arg Lys Lys Arg Arg Arg Glu Ser Glu Cys Lys
GAGCGCCAGGCGCGGGAGCACTCAGAGCGCAAGAAGCGGCGGCGCGAGAGCGAGTGCAAG
CTCGCGGTCCGCGCCCTCGTGAGTCTCGCGTTCTTCGCCGCCGCGCTCTCGCTCACGTTC

Ala Ala
GCCGCC
CGGCGG
``` or any modification thereof encoding a polypeptide which has the superoxide dismutating property of native EC-SOD. It should be noted that the amino acid sequence derived from the DNA sequence is shown above the DNA sequence. Examples of suitable modifications of the DNA sequence are nucleotide substitutions which do not give rise to another amino acid sequence of the protein, but which, for instance, correspond to the codon usage of the specific organism in which the sequence is inserted; nucleotide substitutions which give rise to a different amino acid sequence and therefore, possibly, a different protein structure without, however, impairing the critical property of superoxide radical dismutation; a subsequence of the sequence shown above encoding a polypeptide which has retained the superoxide dismutating property of the native protein; or a DNA sequence hybridizing to at least part of a DNA probe prepared on the basis of the sequence shown above, provided that it encodes a polypeptide which has the biological property of superoxide radical dismutation of the native protein. In this connection, it should be noted that the term "superoxide dismutating property of native EC-SOD" and related terms should be understood to be qualitative rather than quantitative, that is, relating to the nature rather than the level of activity of the polypeptide.

The DNA sequence encoding EC-SOD or modifications or derivatives thereof as defined above may be of complementary DNA (cDNA) origin, that is, obtained by preparing a cDNA library on the basis of mRNA from cells producing EC-SOD by means of established standard methods end vectors. Hybridization experiments may then be carried out using synthetic oligonucleotides as probes to identify the cDNA sequence coding for EC-SOD. Alternatively, the DNA sequence may be of genomic origin, that is, derived directly from a cellular genome, for instance by screening for genomic sequences hybridizing to a DNA probe prepared on the basis of the full or partial amino acid sequence of EC-SOD found in, for instance, tissue in accordance with conventional methods; cf. Example 8 for a more detailed description of the general procedure. Genomic DNA differs from cDNA, for instance by containing transcriptional control elements and the so-called introns which are non-coding sequences within the coding DNA sequence, the significance of which is, at present, obscure. Both cDNA and genomic DNA may be of animal, in particular mammalian, origin. For therapeutic purposes involving human beings, it will usually be preferred that the EC-SOD is EC-SOD encoded by a DNA sequence of human origin, in order to substantially avoid undesirable adverse immune reactions.

The DNA sequence may also be of synthetic origin, i.e. prepared synthetically by established standard methods, e.g. as described by Matthes et al., EMBO Journal 3, 1984, pp. 801–805. Finally, the DNA sequence may be of mixed synthetic and genomic origin, mixed genomic and cDNA origin or mixed cDNA and synthetic origin prepared by ligating together DNA fragments of cDNA, genomic or synthetic origin (as appropriate), which DNA fragments comprise part of the gene encoding EC-SOD, in accordance with standard methods.

Although EC-SOD of recombinant origin is preferred in accordance with the present invention because it is easily available in large quantities, EC-SOD is also available from other sources. Thus, the invention also relates to EC-SOD of cell line origin, i.e. derived from a cell line producing the protein in significant quantities, such as a cell line derived from blood or lung, blood vessel, pancreas, uterus, prostate gland, placenta or umbilical cord tissue or, possibly, neoplastic tissue. Endothelial cells or fibroblasts are at present contemplated to be possible sources of EC-SOD.

Finally, the EC-SOD may also be derived from tissue found to be relatively rich in EC-SOD. Accordingly, the present invention further relates to EC-SOD of placenta or umbilical cord origin as these tissues have been formed to contain reasonably large amounts of EC-SOD compared to other types of tissue, and are also more easily available than, for instance, lung, uterus or pancreas tissue. It should be stressed, however, that even though these tissues contain relatively larger amounts of EC-SOD, these are far smaller than those obtainable by recombinant DNA techniques, and therefore, placenta or umbilical cord EC-SOD is particularly indicated for special purposes requiring only Minor amounts of EC-SOD.

In a further aspect, the present invention relates to a replicable expression vector which comprises a DNA sequence encoding EC-SOD. In the present context, the term "replicable" means that the vector is able to replicate in a given type of host cell into which it has been introduced. The vector may be one carrying the DNA sequence shown above or any suitable modification thereof as explained above. Immediately upstream of this sequence (the coding sequence of EC-SOD) there may be provided a sequence coding for a signal peptide, the presence of which ensures secretion of the EC-SOD expressed by host cells harbouring the vector. The signal sequence may, for instance, be the following sequence:

and might equally well be ascribable to an analytical error. Certainly, a person skilled in the art would not conclude, on the basis of the data presented in this publication, that some of the cell lines tested for their content of EC-SOD might possibly produce EC-SOD as a secreted protein, as there is no indication of this possibility in the article.

The cell line may be of mammalian, in particular human, origin. It is preferable that the cell line is one which produces particularly high quantities (compared to other cells) of EC-SOD. Thus, the cell line may be one which is derived from blood or lung, skin, blood vessel, pancreas, uterus,

```
-18                          -10                               -1
Met Leu Ala Leu Leu Cys Ser Cys Leu Leu Leu Ala Ala Gly Ala Ser Asp Ala
ATGCTGGCGCTACTGTGTTCCTGCCTGCTCCTGGCAGCCGGTGCCTCGGACGCC
TACGACCGCGATGACACAAGGACGGACGAGGACCGTCGGCCACGGAGCCTGCGG
                                                         120
```

It should be noted that this signal sequence (and the signal peptide encoded by it) in itself forms an aspect of the present invention, and it is contemplated that it may be inserted upstream of DNA sequences coding for other proteins or peptides so as to obtain secretion of the resulting products from the cells.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated.

In a further aspect, the invention relates to a cell line which is capable of secreting EC-SOD. While various human cell lines derived from a wide variety of tissue cell as well as tumour cell lines have previously been analysed for their content of EC-SOD (cf. Marklund, *J. Clin. Invest.* 74, October 1984, pp. 1398–1403), no conclusive results were obtained. Although it is mentioned that minor amounts of EC-SOD was found in some of the investigated cell lines, the data presented in Table II of the article are not significant prostate gland, placenta or umbilical cord tissue or, possibly, neoplastic tissue. In particular, it is contemplated that cell lines derived from fibroblasts or endothelial cells are particularly advantageous as sources of EC-SOD, as they are derived from cells directly exposed to extracellular space, which may therefore be assumed to need the protection conferred by EC-SOD from superoxide radicals present or generated in an extracellular environment.

The present invention further relates to a cell harbouring a replicable expression vector as defined above. In principle, this cell may be of any type of cell, i.e. a procaryotic cell such as a bacterium, a unicellular eukaryotic organism, a fungus or yeast, or a cell derived from a multicellular organism, e.g. an animal or a plant. It is, however, believed that a mammalian cell may be particularly capable of expressing EC-SOD which is, after all, a highly complex molecule which cells of lower organisms might not be able to produce. One example of such a cell is CHO-K1/pPS3neo-18 deposited on Aug. 27, 1986 in the European Collection of Animal Cell Cultures under the Accession Number ECACC 86082701.

The invention also relates to a DNA fragment which encodes EC-SOD and which has the following DNA sequence

```
-18                          -10
Met Leu Ala Leu Leu Cys Ser Cys Leu Leu Leu Ala Ala Gly Ala Ser Asp
ATGCTGGCGCTACTGTGTTCCTGCCTGCTCCTGGCAGCCGGTGCCTCGGAC
TACGACCGCGATGACACAAGGACGGACGAGGACCGTCGGCCACGGAGCCTG
                                                         120

-1  +1                       10
Ala Trp Thr Gly Glu Asp Ser Ala Glu Pro Asn Ser Asp Ser Ala Glu Trp Ile Arg Asp
GCCTGGACGGGCGAGGACTCGGCGGAGCCCAACTCTGACTCGGCGGAGTGGATCCGAGAC
CGGACCTGCCCGCTCCTGAGCCGCCTCGGGTTGAGACTGAGCCGCCTCACCTAGGCTCTG
                                                         180

20                          30
Met Tyr Ala Lys Val Thr Glu Ile Trp Gln Glu Val Met Gln Arg Arg Asp Asp Asp Gly
ATGTACGCCAAGGTCACGGAGATCTGGCAGGAGGTCATGCAGCGGCGGGACGACGACGGC
TACATGCGGTTCCAGTGCCTCTAGACCGTCCTCCAGTACGTCGCCGCCCTGCTGCTGCCG
                                                         240
```

```
                                      -continued
   40                              50
Thr Leu His Ala Ala Cys Gln Val Gln Pro Ser Ala Thr Leu Asp Ala Ala Gln Pro Arg
ACGCTCCACGCCGCCTGCCAGGTGCAGCCGTCGGCCACGCTGGACGCCGCGCAGCCCCGG
TGCGAGGTGCGGCGGACGGTCCACGTCGGCAGCCGGTGCGACCTGCGGCGCGTCGGGGCC
                                                                300

60                      70
Val Thr Gly Val Val Leu Phe Arg Gln Leu Ala Pro Arg Ala Lys Leu Asp Ala Phe Phe
GTGACCGGCGTCGTCCTCTTCCGGCAGCTTGCGCCCCGCGCCAAGCTCGACGCCTTCTTC
CACTGGCCGCAGCAGGAGAAGGCCGTCGAACGCGGGGCGCGGTTCGAGCTGCGGAAGAAG
                                                                360

80                      90
Ala Leu Glu Gly Phe Pro Thr Glu Pro Asn Ser Ser Ser Arg Ala Ile His Val His Gln
GCCCTGGAGGGCTTCCCGACCGAGCCGAACAGCTCCAGCCGCGCCATCCACGTGCACCAG
CGGGACCTCCCGAAGGGCTGGCTCGGCTTGTCGAGGTCGGCGCGGTAGGTGCACGTGGTC
                                                                420

100                              110
Phe Gly Asp Leu Ser Gln Gly Cys Glu Ser Thr Gly Pro His Tyr Asn Pro Leu Ale Val
TTCGGGGACCTGAGCCAGGGCTGCGAGTCCACCGGGCCCCACTACAACCCGCTGGCCGTG
AAGCCCCTGGACTCGGTCCCGACGCTCAGGTGGCCCGGGGTGATGTTGGGCGACCGGCAC
                                                                480

120                      130
Pro His Pro Gln His Pro Gly Asp Phe Gly Asn Phe Ala Val Arg Asp Gly Ser Leu Trp
CCGCACCCGCAGCACCCGGGCGACTTCGGCAACTTCGCGGTCCGCGACGGCAGCCTCTGG
GGCGTGGGCGTCGTGGGCCCGCTGAAGCCGTTGAAGCGCCAGGCGCTGCCGTCGGAGACC
                                                                540
  140                      150
Arg Tyr Arg Ala Gly Leu Ala Ala Ser Leu Ala Gly Pro His Ser Ile Val Gly Arg Ala
AGGTACCGCGCCGGCCTGGCCGCCTCGCTCGCGGGCCCGCACTCCATCGTGGGCCGGGCC
TCCATGGCGCGGCCGGACCGGCGGAGCGAGCGCCCGGGCGTGAGGTAGCACCCGGCCCGG
                                                                600

160                              170
Val Val Val His Ala Gly Glu Asp Asp Leu Arg Gly Gly Asn Gln Ala Ser Val Glu
GTGGTCGTCCACGCTGGCGAGGACGACCTGGGCCGCGGCGGCAACCAGGCCAGCGTGGAG
CACCAGCAGGTGCGACCGCTCCTGCTGGACCCGGCGCCGCCGTTGGTCCGGTCGCACCTC
                                                                660

180                      190
Asn Gly Asn Ala Gly Arg Arg Leu Ala Cys Cys Val Val Gly Val Cys Gly Pro Gly Leu
AACGGGAACGCGGGCCGGCGGCTGGCCTGCTGCGTGGTGGGCGTGTGCGGGCCCGGGCTC
TTGCCCTTGCGCCCGGCCGCCGACCGGACGACGCACCACCCGCACACGCCCGGGCCCGAG
                                                                720

200                      210
Trp Glu Arg Gln Ala Arg Glu His Ser Glu Arg Lys Lys Arg Arg Glu Ser Glu Cys
TGGGAGCGCCAGGCGCGGGAGCACTCAGAGCGCAAGAAGCGGCGGCGCGAGAGCGAGTGC
ACCCTCGCGGTCCGCGCCCTCGTGAGTCTCGCGTTCTTCGCCGCCGCGCTCTCGCTCACG
                                                                780

220
Lys Ala Ala ***
AAGGCCGCCTGA
TTCCGGCGGACT
```

It should be noted that this sequence includes the signal-peptide-encoding sequence shown above. The signal sequence extends from amino acid −18 to −1. The sequence encoding mature EC-SOD is initiated at amino acid +1.

The DNA sequence may be of cDNA, genomic or synthetic origin, or of mixed cDNA and genomic, mixed cDNA and synthetic or mixed cDNA and synthetic origin as discussed above.

In a further, important aspect, the present invention relates to a method of producing EC-SOD, in which a cell line producing EC-SOD is grown under conditions ensuring the secretion of EC-SOD. The cell line may be derived from any of the sources mentioned above. Mammalian cells producing EC-SOD may be identified immunohistochemically by means of antibodies directed against EC-SOD or by analysing for EC-SOD secreted into the medium in which specific cells are cultured. The cells may be grown in conventional media adapted to the propagation of cell lines in a manner known per se.

As mentioned above, EC-SOD shows an affinity to heparin which indicates an affinity to heparan sulphate or other heparin-like glucoseaminoglucanes found on cell surfaces, especially on the surface of endothelial cells. It is therefore contemplated to induce the release of EC-SOD from cell surfaces and thereby ensure an improved yield of EC-SOD by growing the tissue cells of the EC-SOD producing cell lines in a medium containing heparin or a heparin analogue, e.g. heparan sulphate, or another sulphated glucoseaminoglycane, dextran sulphate or another strongly negatively charged compound in an amount which is sufficient to induce the release of EC-SOD from the cell surfaces (cf. Example 9-11).

In another important aspect, the invention relates to a method of producing EC-SOD, in which a DNA fragment comprising a DNA sequence encoding EC-SOD is inserted in a vector which is able to replicate in a specific host cell, the resulting recombinant vector is introduced into a host cell which is grown in or on an appropriate culture medium under appropriate conditions for expression of EC-SOD, and the EC-SOD is recovered. The medium used to grow the cells may be any conventional medium suitable for the purpose, but it may be necessary to add extra Cu and/or Zn for the synthesis of EC-SOD, especially if it is to be produced in increased amounts. A suitable vector may be any of the vectors described above, and an appropriate host cell may be any of the cell types listed above. The methods employed to construct the vector and effect introduction thereof into the host cell may be any methods known for such purposes within the field of recombinant DNA. The EC-SOD expressed by the cells may be secreted, i.e. exported through the cell membrane, dependent on the type of cell and the composition of the vector. If the EC-SOD is produced intracellularly by the recombinant host, that is, is not secreted by the cell, it may be recovered by standard procedures comprising cell disrupture by mechanical means, e.g. sonication or homogenization, or by enzymatic or chemical means followed by purification (examples of the recovery procedure are given in Examples 1, 4–6 and 17).

In order to be secreted, the DNA sequence encoding EC-SOD should be preceded by a sequence coding for a signal peptide, the presence of which ensures secretion of EC-SOD from the cells so that at least a significant proportion of the EC-SOD expressed is secreted into the culture medium and recovered. It has been experimentally established that part of the secreted EC-SOD is present in the medium and part of the EC-SOD is present on the cell surfaces. Hence, the expression "secreted into the culture medium" is intended to encompass any transport of the EC-SOD through the cell membrane, whether the enzyme eventually ends up in the culture medium or on the cell surfaces (cf. Examples 9–11). The EC-SOD may be recovered from the medium by standard procedures comprising filtering off the cells and isolating the secreted protein, for instance as outlined in Examples 1, 4–6 and 17. In order to ensure the release of EC-SOD from the cell surfaces, and thus obtain an improved yield, it may be advantageous to add heparin or one of the substances with a similar effect mentioned above to the medium as explained above.

In a still further aspect, the present invention relates to a method of recovering EC-SOD, in which an extract of a biological material containing EC-SOD activity is adsorbed to a matrix containing immobilized antibodies against EC-SOD or an immunological determinant thereof, the EC-SOD activity is eluted from the matrix, and the fractions containing the EC-SOD activity are pooled, optionally followed by further purification. The antibodies employed may be antibodies raised against EC-SOD or an immunological determinant thereof and immobilized on a suitable matrix material in a manner known per se.

The antibodies employed for affinity chromatography according to the invention may either be polyclonal or monoclonal antibodies. The currently preferred antibodies are monoclonal antibodies as most monoclonal antibodies have been found to bind the antigen less strongly than the polyclonal antibody mixture which means that desorption may be carried out under milder conditions with weaker eluants. This may result in an improved yield of EC-SOD as there is a lower degree of denaturation than when strong eluants are used for desorption.

Also, since all the IgG will be directed against EC-SOD, a far smaller amount of antibody matrix will have to be used for the adsorption of EC-SOD from the biological material used as the starting material. The desorption of EC-SOD will require a far smaller volume of eluant, thereby simplifying the elution procedures which are at present inconvenient due to the large volumes of eluant needed for the desorption.

The specificity of monoclonal antibodies for EC-SOD is likely to be higher than that of the polyclonal antibodies. The eluate from the antibody matrix will therefore be purer which means that one or more further purification steps may be omitted. This means that the production procedure will be greatly simplified and a far higher yield of EC-SOD obtained from the same quantity of starting material which presents an important economic advantage.

Polyclonal antibodies may be obtained by immunizing an immunizable animal with EC-SOD or an immunological determinant thereof and obtaining antiserum such as immunoglobulins from the animal in a manner known per se. The immunization is preferably be performed by means of a stabilized aqueous solution of EC-SOD; the stabilization agent may be a buffer such as phosphate buffered saline or an adjuvant (also to further increase the antigenicity), and a suitable adjuvant is Freund's adjuvant or aluminium hydroxide. For immunization purposes, mice, rabbits, hens, goats and sheep are the preferred animals. The bleeding of the animal and the isolation of the antiserum is performed according to well-known methods. The antibody is preferably provided in substantially pure form which is advantageous in order to obtain the necessary purification of the EC-SOD.

When using a monoclonal antibody in the method of the invention, it may be produced by a hybridoma technique which is well-known method for producing antibodies. In the hybridoma technique using, for instance, mice as the animals immunized, mice are immunized with the antigen in question and spleen cells from the immunized mice are fused with myeloma cells whereupon the fused hybridoma cells are cloned, antibody-producing cells are grown in a suitable growth medium and the antibodies are recovered from the culture. The antibodies obtained by the hybridoma technique have the advantage of greater specificity and, hence, a greater purifying potential as mentioned above. In a possible further step, using recombinant DNA techniques, the DNA sequence encoding the antibody is transferred from the hybridoma cell clone to a suitable vector, the hybrid vector is transformed to a suitable bacterial host, the host is grown in an appropriate medium and the resulting antibody is recovered from the culture. In this way, an improved yield of antibody may be obtained. The host may be one usually employed in the field of recombinant DNA technology such as *Eschericia coli* or *Bacillus subtilis*.

In an alternative method of obtaining monoclonal antibodies, the hybridoma cells may be implanted and grown in the abdominal cavity of mice, and the resulting anti-EC-SOD antibodies are recovered from the ascitic fluid produced, in a manner known per se. Furthermore, immunization for obtaining monoclonal antibodies may be performed in vitro using immunocompetent cells from, e.g., mice. In this case it is not necessary to inject an antigen into the animal in question, e.g. a mouse, although this is at present the most commonly employed procedure. It should be noted that monoclonal antibodies and the method of preparing them form one aspect of the invention.

The biological material from which the extract containing the EC-SOD activity is obtained may, for instance, be mammalian tissue. It may be possible to employ bovine, porcine or equine tissue as, for the purpose of comparison, bovine CuZn SOD has been found to have relatively little immunological reactivity in humans and allergic reactions have not been any serious problem. On the basis of this, it may therefore be concluded that the same will be the case for bovine, equine or porcine EC-SOD. It is, however, still preferred to employ human tissue in order to obviate possible undesirable immunological reactions. Human tissue currently preferred for this purpose as it contains relatively large amounts of EC-SOD is human lung, pancreatic, uterine, prostate, umbilical cord or placental tissue, especially the latter two types of tissue, as these are also more easily available. The extract may be prepared in a conventional manner in a suitable buffer such as a phosphate buffer. It has been found advantageous to add a chaotropic salt, e.g. KBr, ammonium sulphate or potassium thiocyanate, to the buffer in order to improve the yield of EC-SOD from the extraction.

However, since EC-SOD is not produced in large quantities in any of those tissues so that very high quantities of tissue will be needed to produce a sufficient amount of EC-SOD for therapeutic purposes, it may be preferred to obtain EC-SOD from an animal, preferably a mammalian, human, cell line which produces EC-SOD. The biological material containing EC-SOD activity may therefore also be the material resulting from growing a cell line producing EC-SOD, as described above. In order to obtain particularly high amounts of EC-SOD, the EC-SOD to be recovered by the methods of the invention may advantageously be produced by recombinant DNA methods as described above.

In most case, especially when employing immobilized polyclonal antibodies for the purification of EC-SOD, the pooled eluate of the antibody matrix may be absorbed to a matrix, e.g. an ion-exchange matrix, followed by eluting the EC-SOD activity from the matrix and pooling fractions containing the EC-SOD activity. Further purification of the pooled eluate may be obtained by applying it on a chromatographic column of a matrix comprising heparin or a heparin analogue, e.g. heparan sulphate, or another sulphated glucoseaminoglycane, dextran sulphate or another strongly negatively charged compound and eluting followed by pooling the fractions showing affinity to the substance in question.

In a yet further, very important aspect, the present invention relates to the use of EC-SOD for the diagnosis, prophylaxis or treatment of diseases or disorders connected with the presence or formation of superoxide radicals and other toxic oxygen intermediates derived from the superoxide radical.

Examples of such diseases or disorders are selected from conditions involving ischaemia followed by reperfusion, e.g. infarctions such as heart, kidney, brain or intestine infarctions, inflammatory diseases such as rheumatoid arthritis, pancreatitis, in particular acute pancreatitis, pyelonephritis and other types of nephritis, and hepatitis, autoimmune diseases, insulin-dependent diabetes mellitus, disseminated intravascular coagulation, fatty embolism, adult respiratory distress, infantile respiratory distress, brain haemorrhages in neonates, burns, adverse effects of ionizing radiation, and carcinogenesis.

Thus, EC-SOD is indicated for substantially the same applications as CuZn SOD the therapeutic activity of which has been more thoroughly documented as discussed below.

EC-SOD, however, has been found to possess a number of characteristics which are assumed to make it particularly useful for therapeutic applications. CuZn SOD has a low molecular weight (33,000) which causes it to become eliminated very quickly by glomerulus filtration in the kidneys so that, in human beings, the enzyme has a half-life of only about 20–30 minutes. Preliminary experiments with EC-SOD have surprisingly established a significantly longer half-life of EC-SOD (in rabbits), cf. Example 10. This is currently believed partly to be ascribable to the high molecular weight of EC-SOD, 135,000, which prevents it from being eliminated by glomerulus filtration, and partly to the fact that EC-SOD seems to bind to endothelial cell surfaces as indicated below. In the therapeutic use of EC-SOD according to the invention, the enzyme therefore preferably has a half-life in human beings of at least 4 hours and possibly even longer.

As explained above, EC-SOD is, in its native environment, a secreted protein and it is therefore likely that it is specifically synthesized for a function in extracellular space (in extracellular fluids or on cell surfaces) which may cause it to exhibit properties which are particularly well adapted to protect plasma components or the outer surface of cells against the toxic effects of superoxide radicals or other oxygen radicals. This suggestion is supported by the findings that EC-SOD has a slightly hydrophobic character which may cause it to have a tendency to bind to the outer surface of cells, and that it shows affinity to heparin indicating an affinity to heparan sulfate which is found on the outer surface of cells, both of which qualities would seem to indicate a particularly good ability to protect tissue, cf. Example 9, 10 and 11 in which the test results seem to verify the binding of EC-SOD to blood vessel endothelium.

The significance of the apparent association of EC-SOD with cell membranes is further supported by the finding that CuZn SOD which has been modified with polylysine to bind to cell membranes is better able to protect activated (superoxide radical-producing) polymorphonuclear leukocytes (PMN) from autoinactivation (cell death) than normal CuZn SOD which is negatively charged and therefore tends to be repelled by the cell membranes (M. Salin and J. M. McCord, "Free radicals in leukocyte metabolism and inflammation", in *Superoxide and Superoxide Dismutases*, eds. A. M. Michelson, J. M. McCord and I. Fridovich, Academic Press, 1977, pp. 257–270). The fact that *Nocardia asteroides* possesses a membrane-associated SOD which appears to confer efficient protection against activated human PMNs as the susceptibility of Nocardia to PMNs is significantly increased when Nocardia cells are treated with antibodies towards this SOD (B. L. Beaman et al., *Infection and Immunity* 47, 1985, pp. 135–141) also points to a cell membrane-protective function of SOD bound to cell surfaces. Unlike EC-SOD, CuZn SOD has an intracellular function which may make it less well suited for extracellular application, i.e. occasioned by the extracellular presence of superoxide radicals. Furthermore, its brief half-life compared to that of EC-SOD mentioned above would seem to make it necessary to administer larger doses at shorter intervals that is likely to be the case with EC-SOD.

SOD activity for potential therapeutic applications has been demonstrated for the following diseases or disorders.

Parenterally administered CuZn SOD has been shown to exhibit an anti-inflammatory effect in a series of animal models of inflammation as well as in inflammatory diseases in animals (Huber and Saifer, in *Superoxide and Superoxide Dismutases*, eds. Michelson et al., Academic Press, 1977, pp. 517–549). In humans, positive effects of CuZn SOD has been reported in rheumatoid arthritis and arthroses, in inflammation of the bladder and other urological conditions (Menander-Huber in *Biological and Clinical Aspects of Superoxide and Superoxide Dismutase*, eds. Bannister et al., Elsevier/North Holland, 1980, pp. 408–423) as well as adverse effects of treatment with ionizing radiation (Edsmyr et al., *Current Therapy. Res.* 10, 1976, pp. 198–211; Cividalli et al., *Acto. Rodiol. Oncol.* 24, 1985, pp. 273–277 (in rats)); in some countries, bovine CuZn SOD has become registered as a drug (Orgotein, Peroxinorm), employed mainly for the treatment of arthritis and arthroses where the composition is administered intraarticularly (Goebel and Storck, Am. J. Med. 74, 1983, pp. 124–128).

Parenterally administered CuZn SOD is not taken up by the cells and must exert its activity in extracellular space. CuZn SOD encapsulated in liposomes is taken up by the cells and is reported to be effective against Crohn's disease, Bechet's disease, dermatitis herpetiformis, ulcerative colitis, Kawasaki's disease and against the adverse effects of radiation therapy (Y. Niwa et al., Free Rod. Res. Comms. 1, 1985, pp. 137–153). The mechanism of the anti-inflammatory activity of CuZn SOD is not quite clear. Direct protection against oxygen radicals formed by activated leucocytes has been suggested (Halliwell, Cell Biol. Int. Rep. 6, 1982, pp. 529–541). Another possibility is prevention of the formation of a superoxide induced strongly chemotaxic substance (Petrone et al., Proc. Natl. Acad. Sci. USA 77, 1980, pp. 1159–1163).

The other large potential area of application for SOD is as a protective factor against tissue damage caused by ischaemia followed by reperfusion. If the supply of blood to a tissue is cut off, the tissue will slowly become necrotic. Macro- and microscopically the damage will typically develop slowly over several hours. If the tissue is reperfused after, for instance, one hour, a strong acceleration of the tissue damage will occur instead of an improvement. Most likely there are several reasons for this so-called reperfusion paradox, but oxygen radicals formed as a result of the reappearance of oxygen in previously ischaemic tissue appear to contribute to the damage. Since the radicals are extremely shortlived and therefore difficult to study directly, their formation and effects may be inferred from the protective action of various scavengers. Tissue protection (by means of a protective substance) has been demonstrated in ischaemia- or anoxia-reperfusion models in the kidney (SOD [G. L. Baker et al., Am. Surg. 202, 1985, pp. 628–641; I. Koyama et al., Transplantation 40, 1985, pp. 590–595], SOD, catalase [E. Hansson et al., Clin. Sci. 65, 1983, pp. 605–610] and allopurinol [G. L. Baker et al., op. cit.; I. Koyama et al., op. cit.]) intestine (SOD [D. A. Parks et al., Gastroenterology 82, 1982, pp. 9–15; M. H. Schoenberg et al., Acta Chim. Scand. 150, 1984, pp. 301–309; M. C. Dalsing et al., J. Surg. Res. 34, 1983, pp. 589–596] and allopurinol [D. A. Parks et al., op. cit.]), pancreas (SOD, SOD+catalase, catalase and allopurinol [H. Sanfey et al., Ann. Surg. 200, 1983, pp. 405–413]), liver (SOD and catalase [S. L. Atalla et al., Transplantation 40, 1985, pp. 584–589], lung (SOD+catalase [R. S. Stuart et al., Transplant. Proc. 17, 1985, pp. 1454–1456]) skeletal muscle (SOD, catalase and allopurinol [R. V. Korthuis, Circ. Res. 57, 1985, pp. 599–609]), skin (SOD and allopurinol [M. J. Im et al., Ann. Surg. 201, 1985, pp. 357–359]) and brain (SOD and allopurinol [J. S. Beckmann et al., in Superoxide and Superoxide Dismutase in Chemistry, Biology and Medicine, ed. G. Rotilio, Elsevier, 1986, pp. 602–607]).

Preservation of heart function has been reported in isolated, perfused preparations from the rabbit (catalase, allopurinol; SOD had no effect [C. L. Myers et al., J. Thorac. Cardiovasc. Surg. 91, 1986, pp. 281–289]), cat (SOD+ catalase [M. Schlafer et al., Circulation 66, Suppl. I, 1982, pp. 185–192]) and rat (glutathione, catalase, SOD Gaudel et al., J. Mol. Cell Cardiol. 16, 1984, pp. 459–470]). In regional ischaemia-reperfusion models in vivo, reduction of infarct size has been reported in the dog (SOD [T. J. Gardner et al., Surgery 94, 1983, pp. 423–427; D. E. Chambers et al., J. Mol. Cell Cardiol. 17, 1985, pp. 145–152; S. W. Werns et al., Circ. Res. 56, 1985, pp. 895–898]), and allopurinol [D. E. Chambers et al., op. cit.; T. J. Gardner et al., op. cit.], catalase had no effect [S. E. Werns et al., op. cit.] Injection of SOD+catalase has also been reported to preserve the mechanical heart function after a brief (15 minutes) regional ischaemia in the dog (M. L. Myers et al., Circulation 72, 1985, pp. 915–921; K. Przyklenk and R. A. Kloner, Circ. Res. 58, 1986, pp. 148–156). Furthermore, SOD has been reported to reduce the incidence of ischaemia-and-reperfusion induced arrythmias (B. Woodward et al., J. Mol. Cell. Coriol. 17, 1985, pp. 485–493; M. Bernier et al., Circ. Res. 58, 1986, pp. 331–340). The source of oxygen radicals in this situation is not completely clear, but the effect of allopurinol seems to indicate that it is partly caused by xanthine oxidase which, by ischaemia, is converted from its xanthin dehydrogenase form (Parks et al., op. cit.) to the radical-producing oxidase form. A large amount of hypoxanthine which is the substrate for xanthine oxidase is formed due to purine nucleotide degradation induced by ischaemia. Other sources of superoxide radicals may be activated leukocytes attracted to ischaemia-damaged tissue, prostaglandin synthesis ($O_2^-$ is a byproduct; Kontos, Circ. Res. 57, 1985, pp. 508–516) and autooxidation of various compounds accumulated in reduced form during ischaemia. The finding concerning ischaemia followed by reperfusion has potentially important clinical applications. It may be possible to obtain an excellent effect by reperfusion of tissue in connection with heart infarctions, by the concomitant administration of an SOD and/or other protective factors against oxygen radicals and thrombolytic factors, e.g. tissue plasminogen activator. The results of the SOD experiments also indicate a possible application in connection with heart surgery and heart transplantations. Analogously, the results of employing an SOD in connection with kidney ischaemia followed by reperfusion may be employed in connection with kidney transplantations and other organs transplantations such as skin, lung, liver, or pancreas transplantations. Ischaemia brain disease is another possible indication.

SODs show interesting protective effects in connection with other pathological conditions.

Thus, pancreatitis was induced in dog pancreas in three different ways: infusion of oleic acid, partial obstruction of the excretory ducts and ischaemia followed by reperfusion. SOD, catalase, and SOD+catalase were found to be protective, the combination treatment being generally the most effective. In the ischaemia model, however, SOD alone was almost as effective as the combination of SOD and catalase (Sanfey et al., Ann. Surg. 200, 1984, pp. 405–413). SOD+catalase has been reported to ameliorate pancreatitis induced by cerulein in rats (K. S. Guice et al., Am. J. of Surg. 151, 1986, pp. 163–169). The results indicate the possibility of an active therapy against this disease for which no specific therapy exists at present.

It has also been suggested that treatment with SOD is effective against burns. The local oedema after an experimental slight burn in rats could be somewhat decreased through injection of SOD (Björk and Artursson, Burns 9, 1983, pp. 249–256). In an animal model involving severe burn damage of mice a dramatic protection was obtained by means of SOD, where survival and local damage were concerned (Saez et al., Circulatory Shock 12, 1984, pp. 220–239).

In the case of, for instance, burns, immunocomplex formation, and major tissue damage, neutrophilic leukocytes are accumulated in the lungs. Complement activation (C5 a) often seems to mediate the accumulation. The leukocytes seem to be activated and release oxygen radicals, thereby causing lung damage which, for instance, is characterized by increased vessel permeability and lung oedema (adult respiratory distress). In several animal models, SOD and other oxygen radical scavengers have been shown to have a protective effect against lung damage (Till and Ward, *Agents and Actions, Suppl.* 12, 1983, pp. 383–396).

Parenterally administered CuZn SOD has been reported to prevent bronchopulmonary dysplasia in preterm neonates suffering from infantile respiratory distress (W. Rosenfeld et al., *J. Pediatr.* 105, 1984, pp. 781–785).

In a beagle puppy model, injection of SOD has been reported to reduce the frequency of intraventricular brain haemorrhage following hypotension (L. R. Ment et al., *J. Neurosurg.* 62, 1985, J63–J69).

SOD ameliorates hepatitis in rats induced by injection of *Corynebacterium parvum* (M. J. P. Arthur et al., *Gastroenterology* 89, 1985, pp. 1114–1122).

The endothelium-derived vessel relaxant factor is very sensitive to superoxide, and administration of SOD augments its actions (R. J. Gryglewski et al., *Nature* 320, 1986, pp. 454–456; G. M. Rubanyi et al., *Am. J. Physiol.* 250, 1986, pp. H822–H827). Superoxide radical production can occur under many circumstances in the body and may cause vasoconstriction and decreased tissue perfusion. Administration of SOD is believed to be able to relieve such vasoconstriction.

Acute severe increase in blood pressure leads to functional and morphologic absormalities in brain arterioles. Prostaglandin synthesis inhibitors and superoxide dismutase is contemplated to protect against the abnormalities. Superoxide release can be detected (H. A. Kontos, *Circ. Res.* 57, 1985, pp. 508–516). Close analysis of the model has lead to the conclusion that superoxide radicals are formed as a by-product during prostaglandin synthesis. The results suggest that tissue damage caused by superoxide radicals released during prostaglandin synthesis may occur in other pathological situation and that SOD may exert a protective action.

CuZn SOD+catalase in the medium have been reported to prolong the survival of the perfused isolated rabbit cornea (O. N. Lux et al., *Curr. Eye Res.* 4, 1985, pp. 153–154). CuZn SOD+catalase protect the isolated less against photoperoxidation (S. D. Varma et al., *Ophtholmic Res.* 14, 1982, pp. 167–175). The results suggest possible beneficial effects of SOD in cornea transplantations and other opthalmic surgical procedures.

Ameliorative action of parenteral SOD has been reported in animal models of such acute conditions as disseminated intravascular coagulation (T. Yoshikawa et al., *Thromb. Hoemostas.* 50, 1983, pp. 869–872) and septicemia (H. F. Welter et al., *Chirurgisches Forum '85 f. experim. u. klinischer Forschung*, Springer-Verlag, Berlin, 1985).

In various types of autoimmune disease, such as systemic lupus erythematosus (SLE), systemic sclerosis and rheumatoid arthritis, an increased frequency of chromosomal breaks in lymphocytes has been demonstrated (Emerit, "Properties and action mechanisms of clastogenic factors", in *Lymphokines*, Vol. 8, ed. E. Pick, Academic Press, 1983, pp. 413–424). Fibroblast cultures and direct bone marrow preparations also sometimes show increased breakage. Plasma from such patients contains a chromosome breaking—clastogenic—factor. In some instances a similar factor has also been demonstrated in synovial fluid and in cerebrospinal fluid (disseminated sclerosis). Breaks occur in normal lymphocytes which are cocultivated with lymphocytes from patients with autoimmune disease. Lymphocytes from patients condition culture media to produce chromosome breaks. The clastogenic activity of SLE plasma can be increased by UV-irradiation. Production of superoxide in plasma by means of xanthine oxidase and xanthine results in formation of clastogenic activity. In all the above described models, addition of CuZn SOD to the medium protected against the clastogenic activity (Emerit, ibid.). This indicates that superoxide radicals are involved in both the formation and actions of the clastogenic factor (Emerit, ibid.).

In an animal model of SLE, the New Zealand black mouse which possesses the clastogenic factor, the chromosomes are protected in bone marrow cells in vivo by repeated injections of SOD (Emerit et al., *Cytogenet. Cell Genet.* 30, 1982, pp. 65–69). It is, however, still unclear to what extent the clastogenic factor contributes to the major symptoms in human autoimmune disease and whether administration of SOD has any therapeutic effect.

The neoplastic transformation of cells is usually divided into two phases, i.e. initiation followed by promotion. In in vitro models where initiation has been caused by ionizing radiation, bleomycin, misonidazole and other nitroimidazoles the oncogenic transformation has been effectively inhibited by the presence of SOD in the medium. It is not necessary for SOD to be present during exposure to the initiating substances which seems to indicate that the enzyme inhibits the subsequent promotion step (Miller et al., *Int. J. Radiot. Oncol. Biol. Phys.* 8, 1982, pp. 771–775; Borek and Troll , *Proc. Not. Acad. Sci. USA* 80, 1983, pp. 1304–1307). Non-toxic doses of xanthine+xanthine oxidase causes promotion in growing cells. Addition of SOD or SOD+catalase inhibits this effect (Zimmerman and Cerutti, *Proc. Nat. Acad. Sci. USA* 81, 1984, pp. 2085–2087). Phorbol esters are known promoters. In a model in which skin tumors were induced by initiation with a benzanthracene followed by application of a phorbol ester (TPA), local treatment with a lipophilic copper complex with SOD activity strongly reduced tumor formation (Kenzler et al., *Science* 221, 1983, pp. 75–77). The result indicates that, at least in certain cases, superoxide radicals contribute to the promotion of tumor formation and that SOD may protect against this effect.

There is reason to believe that oxygen radicals contribute to the damaging effects of a number of toxic substances such as bleomycin, adriamycin, alloxan, 6-hydrodopamine, paraquat, dihydroxyfumaric acid, nitrofurantoin and streptozotocin. In those cases where radical formation takes place in the extracellular space it might be possible to protect by means of injected protective enzyme. Thus, SOD may protect against the diabetogenic activity of alloxan (damages β-cells in the pancreas) in vitro (Grankvist et al., *Biochem. J.* 782, 1979, pp. 17–25) and in vivo (Grankvist et al., *Nature* 294, 1981, pp. 158–160). The damaging effect of alloxan seems therefore to be mediated by the superoxide radical or by other oxygen radicals derived from it. The reason for the great sensitivity of the β-cells to alloxan is not clear, and it has been speculated whether there is any connection between alloxane sensitivity and the incidence of insulindependent diabetes mellitus. In diabetes mellitus there is an infiltration in the Langerhans' islets by inflammatory cells which potentially may form oxygen radicals. It may therefore be contemplated to protect the β-cells by injections with SOD at the first onset of diabetes mellitus.

It has been reported (Mossman and Landesman, *Chest* 835, 1983, pp. 50s–51s) that SOD added to the growth medium protects tracheal cells against asbestos.

It has been described (Roberts et al., *J. Urol.* 128, 1982, pp. 1394–1400) that parenteral CuZn SOD protects kidneys against experimentally induced pyelonefritis. SOD and, in particular, catalase protect against acute nephrotoxic nephritis induced in rats by antiglomerular basement membrane antibodies (A. Rehan et al., *Lab. Invest.* 51, 1984, pp. 396–403).

Generally, CuZn SOD has been employed as the test substance in the experiments described above. It is, however, assumed that EC-SOD may be employed for the same purposes and, as has been indicated above, with greater efficiency due to its particular properties which may make it especially attractive to employ EC-SOD extracellularly.

The present invention further relates to a pharmaceutical composition which comprises EC-SOD together with a pharmaceutically acceptable excipient, diluent or vehicle. The EC-SOD incorporated in the composition may be from any of the sources discussed above, i.e. of recombinant, cell line or tissue origin.

The estimate of a suitable, i.e. therapeutically active, dosage for systemic treatment is made on the basis of the content of EC-SOD in the human body. EC-SOD is the major SOD in human plasma, and the total activity (composed of fractions A, B, and C, cf. Example 2) is about 20 U/ml. Injection of 200 IU heparin per kg body weight results in an increase of EC-SOD fraction C of about 23 U/ml, cf. Example 9. Although this heparin dosage is very high, a maximum release was apparently not achieved, cf. Example 9. Assuming that approximately twice as much EC-SOD fraction C may be released from vessel endothelium, the total EC-SOD content in vessels would correspond to about 66 U/ml plasma (20+2×23 U/ml). The total plasma volume is about 4.7% of the body weight corresponding to about 3.3 l in a 70 kg person. 1 unit EC-SOD equals about 8.8 ng. The total amount of EC-SOD in the blood vessels (plasma and vessel endothelium) is therefore 3300×66×8.8×10$^{-9}$ g=1.92 mg. A tenfold increase would require 19 mg and a 300-fold increase 575 mg EC-SOD C. A suitable dosage of EC-SOD may therefore be in the range of about 15–600 mg/day, dependent, i.a. on the type and severity of the condition for which administration of EC-SOD is indicated. Injection of, for instance, 87 mg EC-SOD C (a 50-fold increase) would result in 26 µg/ml in plasma (disregarding endothelium binding). This or even lower concentrations show strong protective properties in in vitro experiments (with CuZn SOD) (cf. A. Baret, I. Emerit, *Mutation Res.* 121, 1983, pp. 293–297; K. Grankvist, S. Marklund, J. O. Sehlin, I. B. Täljedal, *Biochem. J.* 182, 1979, pp. 17–25).

The dosage and timing of EC-SOD injections depends on the half-life of the enzyme in human blood vessels, which is not yet known. In rabbits human EC-SOD displayed a half-life of about 18 h (cf. Example 10). The half-life in humans is probably longer. Assuming first-order kinetics and a half-life of 36 h, daily injections of 35 mg after an initial injection of 87 mg would therefore result in the same concentration as after the initial injection.

Example 9 shows that EC-SOD C can be mobilized from cell surfaces to plasma with heparin. Parenteral heparin, other sulphated glucoseaminoglycans and other strongly negatively charged substances may be used to modulate the location of endogenous or injected EC-SOD C (cf. Example 9–11). Localization to the plasma phase might be useful in certain pathological conditions.

EC-SOD is composed of three fractions, A without, B with weak and C with strong heparin-affinity. The reasons for the different affinities are not known yet, but the fractions are in most respects very similar. Electrophoresis in PAGE-SDS gels reveals no differences, the amino acid compositions appear to be identical (S. Marklund, *Proc. Natl. Acad. Sci. USA* 79, 1982, pp. 7634–7636) and antibodies raised against A and C seem to react equally with all three fractions (S. Marklund, *Biochem. J.* 220, 1984, pp. 269–272). The fractions may be produced by the same gene, and be modified posttranslationally. All three fractions exist in fresh plasma (cf. Example 9) and is the fraction, the pharmacokinetics of which is discussed above. C is also the fraction produced by recombinant DNA techniques (cf. Example 13). However, it is contemplated that EC-SOD fractions A and B may also be therapeutically useful in pathological conditions in which high SOD activity in solution is important.

For topical treatment, far less EC-SOD than indicated above will probably be needed. At present, 4–8 mg of CuZn SOD are administered intraarticularly once a week for the treatment of arthritis. EC-SOD which has a far higher molecular weight is likely to remain in the joint for a longer period of time. A similar treatment protocol or possibly somewhat lower doses will probably be appropriate.

Before use, the EC-SOD-containing composition should preferably be dry-stored, e.g. in lyophilized form. For systemic treatment and local injections the EC-SOD may suitably be formulated for parenteral administration, e.g. dissolved in an appropriate, non-toxic, physiologically acceptable solvent such as isotonic saline. For topical application, the pharmaceutical composition may be in the form of, for instance, an ointment, lotion, spray, cream or aerosol containing EC-SOD.

It is further contemplated that, in the pharmaceutical composition of the invention, EC-SOD may advantageously be combined with catalase which dismutates hydrogen peroxide in the following way:

$$H_2O_2 + H_2O_2 \xrightarrow{catalase} O_2 + 2H_2O$$

The combined action of EC-SOD and catalase further reduces the formation of the hydroxyl radical which, as described above, is thought to be the most toxic of the oxygen radicals. Instead of catalase, another antioxidant which cooperates with EC-SOD to reduce the toxic effects of oxygen reduction products may be employed.

It is also contemplated that combinations of EC-SOD and other substances such as allopurinol (inhibits xanthine oxidase), scavengers of the hydroxyl radical (e.g. mannitol or compounds containing the sulfhydryl group) and chelators of transition metal ions (e.g. desferrioxamine) may be advantageous.

Moreover, for applications where the presence of EC-SOD in plasma is indicated, it may be advantageous to incorporate heparin or a heparin analogue, e.g. heparan sulphate or another sulphated glucoseaminoglycane, dextran sulphate or another strongly negatively charged compound, in the composition in order to mobilize the EC-SOD present on cell surfaces in the patient to be treated, thereby providing an extra dosage of EC-SOD in the plasma.

The invention also relates to a method of preventing or treating a disease or disorder connected with the presence or formation of superoxide radicals, comprising administering, to a patient in need of such treatment, a therapeutically or prophylactically effective amount of EC-SOD. The disease or disorder may be any one of those discussed above. The invention also relates to a method of preventing or treating damage caused by ischemia followed by reperfusion in connection with the transplantation of organs such as kindney, lung, pancreas, heart, liver or skin, or in connection with heart surgery, comprising administering a therapeutically or prophylactically effective amount of EC-SOD before, during or after surgery. In either method, a therapeutically or prophylactically active dosage may comprise about 15–600 mg/day of EC-SOD, dependent i.a., on the type and severity of the condition to be treated. It may be advantageous, in this method, to co-administer heparin or another strongly negatively charged compound as discussed above, and/or catalase or an antioxidant with a similar effect as also discussed above.

DESCRIPTION OF THE DRAWINGS

The invention is further described with reference to the drawings, in which

FIG. 5a and 5b show the DNA sequence and deduced amino acid sequence of EC-SOD (cf. Example 8).

EXAMPLE 1

Preparation of Umbilical Cord Homogenates

Figure 1:
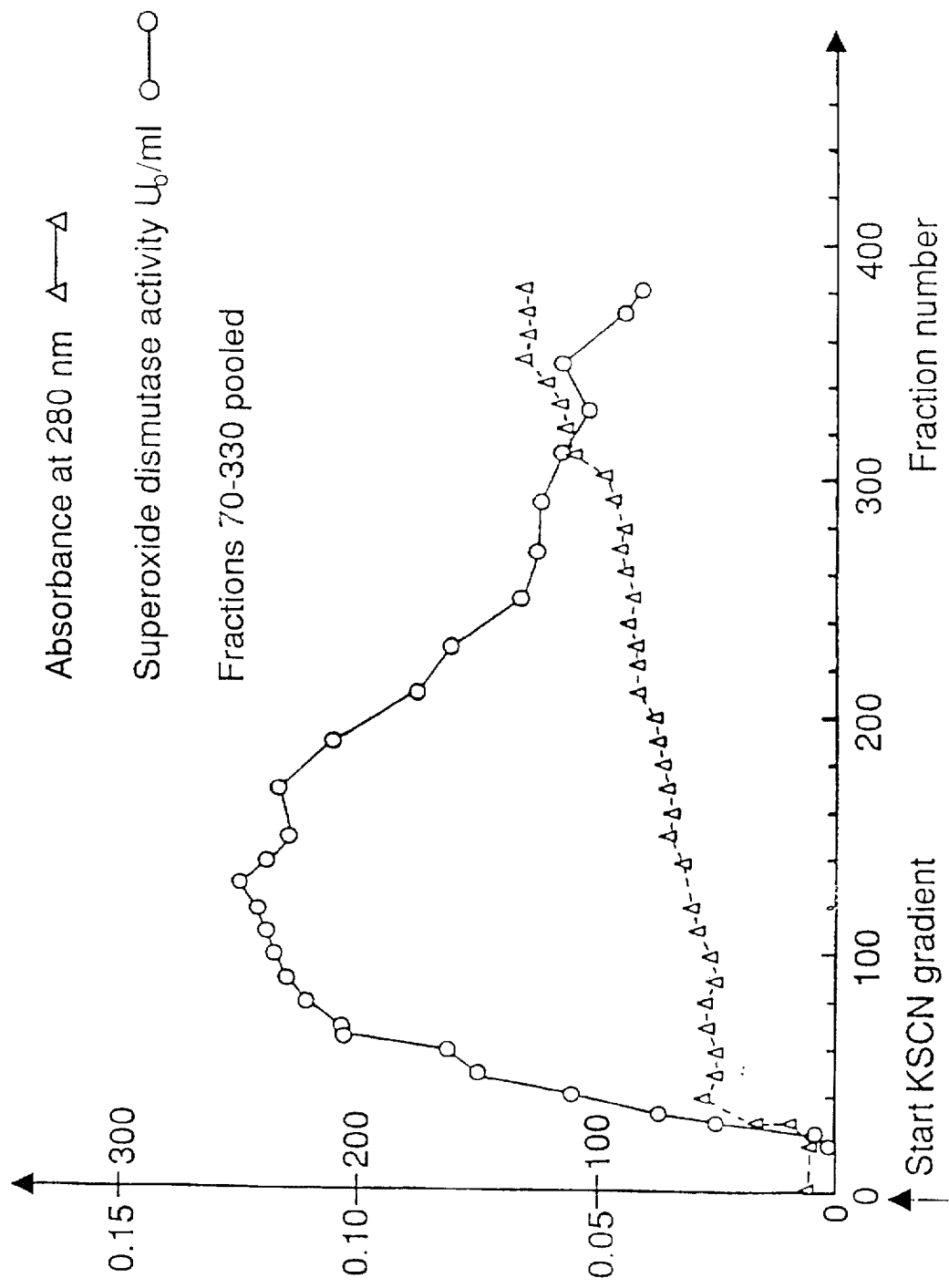
FIG. 1 is a graph showing the elution pattern of protein and EC-SOD after immunoadsorption of an EC-SOD-containing material to anti-EC-SOD-Sepharose® (cf. Example 4).

Human umbilical cords were collected at the maternity ward of Umea University Hospital. They were kept in a refrigerator at the ward and frozen rapidly at the laboratory at −80° C. and then stored at −30° C. before use.

After thawing, the umbilical cords were minced. They were then suspended in 50 ml of K phosphate buffer, pH 7.4, containing 0.3M KBr, 3 mM DTPA, 100,000 kIU/l Trasylol® (aprotinin) and 0.5 mM phenylmethylsulphonylfluoride (PMSF). 4 l of buffer per kg of umbilical cord were employed. The chaotropic salt KBr was used to increase extraction of EC-SOD from the tissue (about 3-fold). DTPA, Trasylol® and PMSF were added to inhibit proteases. The suspension was then homogenized in a Waring blender and finally treated with a sonicator. It is then shaken at 4° C. for 1 hour. The resulting homogenates were centrifuged (6000× g, 20 min.), and the supernatants were rapidly frozen at −80° C. and finally kept at −30° C.

EXAMPLE 2

Preparation and Purification of Human Lung EC-SOD

Human lungs were obtained, within 24 hours after death, at autopsy from nine patients without any apparent lung disease. The lungs were cut into pieces and excess blood was washed away in 0.15M NaCl. The pieces were homogenized in a Waring blender in 5 volumes of ice-cold 50 mM Na acetate at pH 5.50. The homogenate was then sonicated, allowed to extract for 30 minutes at 4° C., and finally centrifuged (6,000×g) for 20 minutes.

The supernatant was batch-adsorbed on DEAE-Sephacel® (obtained from Pharmacia, Uppsala, Sweden) (1 volume per 25 volumes of homogenate) equilibrated with 50 mM Na acetate at pH 5.50. The ion exchanger was then washed with the buffer, packed in a column, and eluted with a gradient of 0–200 mM NaCl in the acetate buffer. The gradient volume was 10 times the column volume.

The active fractions from the previous step were pooled, diluted with 1.5 volumes of distilled water, and titrated to pH 8.4 with 1M NaOH. The pool was again batch-adsorbed to DEAE-Sephacel® equilibrated with 175 mM Tris·HCl at pH 8.4 (=1 volume of ion exchanger per 10 volumes of pool). The DEAE-Sephacel® was subsequently washed with the buffer, packed in a column and, eluted with 10 column volumes of a 0–200 mM NaCl gradient in the Tris buffer.

The pooled fractions from the previous step were concentrated and dialyzed against 150 mM Na phosphate at pH 6.5. The sample was applied to a column (about 1 ml of gel per 15 mg of protein in the sample) with Phenyl-Sepharose® (obtained from Pharmacia, Uppsala, Sweden) equilibrated against the same buffer. The activity was eluted with 20 column volumes of a 0–0.5M KBr gradient in 50 mM Na phosphate at pH 6.5.

Active fractions from phenyl-Sepharose® were pooled, concentrated, and dialyzed against 0.15M Na phosphate at pH 6.5. The sample was applied to a column of Con A-Sepharose® (obtained from Pharmacia, Uppsala, Sweden) (1 ml of gel per 2 mg of protein in the sample), equilibrated against the phosphate buffer, and then pulse-eluted with 50 mM α-methyl D-mannoside in the phosphate buffer.

Active fractions from the Con A-Sepharose® were pooled, concentrated, applied to an Ultrogel ACA-34 column (2.5×83 cm) (obtained from LKB, Stockholm, Sweden), and eluted in 50 mM Na phosphate at pH 6.5. The elution rate was 5 ml·h$^{-2}$.

Active fractions from the elution were pooled, concentrated, and applied to a wheat germ lectin-Sepharose® column (10 ml) (obtained from Pharmacia, Uppsala, Sweden) equilibrated with 0.15M Na phosphate at pH 6.5. The enzyme was pulse-eluted with 0.45M N-acetyl-D-glucosamine in the phosphate buffer.

Active fractions from the above step were pooled, concentrated, dialyzed against 0.15M Na phosphate at pH 6.5, and applied to a blue Sepharose® CL-6B (Cibacron Blue F3G-A) column (bed volume 6 ml) (obtained from Pharmacia, Uppsala, Sweden) equilibrated with the phosphate buffer. After washing the column with buffer, a pulse of 10 mM NAD and 10 mM NADP in the buffer was introduced. After the pyridine nucleotides had been washed out with buffer, the enzyme was pulse-eluted with 0.9M KBr/50 mM Na phosphate, pH 6.5.

The active fractions from the blue Sepharose® column were pooled, dialyzed against 25 mM Na phosphate at pH 6.5, and applied to a heparin-Sepharose® column (bed volume, 10 ml) (obtained from Pharmacia, Uppsala, Sweden) equilibrated with the same buffer. The column was then eluted with 140 ml of a 0–1M NaCl gradient in the phosphate buffer. The activity eluted in three distinct peaks: A did not bind to the heparin, B desorbed early in the gradient, and C desorbed late.

Peak A contained UV-absorbing material which probably had leaked from the heparin-Sepharos® column and was further purified on a Sephacryl® S-300 column (1.6×90 cm) (obtained from Pharmacia, Uppsala, Sweden). The sample was eluted in 25 mM Tris·HCl at pH 7.5.

Fractions A, B, and C were dialyzed against 25 mM Tris·HCl at pH 7.5 and then concentrated to about 1 ml on Amicon UM-10 ultrafiltration membranes. Fraction C was employed to produce EC-SOD antibodies as described in the following example.

EXAMPLE 3

Preparation of Rabbit-Anti-Human EC-SOD

EC-SOD, fraction C, was prepared as described in Example 2. A rabbit was subcutaneously injected with 30 μg of EC-SOD in Freund's complete adjuvant. The immunization was then boostered with 5 injections of 30 μg of EC-SOD in Freund's incomplete adjuvant at intervals of one month. 2 weeks after the last booster dose, the rabbit was bled to death and the serum collected. The IgG fraction of the antiserum was isolated by adsorption and desorption from Protein A-Sepharose® as recommended by the manufacturer (Pharmacia, Uppsala, Sweden). The elution from the column was performed with 0.1M glycine-HCl pH 3.0. Immediately after elution, the pooled IgG was titrated to pH 7.0. The IgG was thereafter dialyzed against 0.1M Na carbonate, pH 8.3+0.15M NaCl, "coupling buffer".

The CNBr-activated Sepharose® was swollen and prepared as recommended by the manufacturer (Pharmacia, Uppsala, Sweden). The IgG as described above was diluted to about 5–8 mg/ml with "coupling buffer". CNBr-activated Sepharose® was added and the mixture incubated with shaking overnight at 4° C. About 5 mg IgG per ml gel was coupled. The buffer was sucked off from the gel and analysed for remaining protein. Over 98% coupling is generally achieved. The IgG-coupled gel was then blocked by suspension in 1M ethanolamine overnight at 4° C. Then the gel was washed with "coupling buffer", followed by 0.1M Na acetate, pH 4.0+0.5M NaCl. The gel was then kept in "coupling buffer" with azide as antibacterial agent.

The maximum binding capacity of the immobilized antibodies was determined by incubation overnight with an excess of EC-SOD and analysis of the remaining EC-SOD. After centrifugation the result was compared with a sham incubation with Sepharose® 4B.

100 μl of a 50% suspension of anti-EC-SOD-Sepharose was added to 0.5 ml EC-SOD in "coupling buffer". A parallel sham incubation with 100 μl of a 50% suspension of Sepharose® 4B was performed. The solutions were shaken overnight at 4° C. and then centrifuged. The remaining activity in the Sepharose® 4B-treated solution was 2080 U/ml and in the anti-EC-SOD-Sepharose-treated solution it was 720 Units/ml. Using these figures it could be calculated that 1 ml of anti-EC-SOD-Sepharose gel bound 13500 units of EC-SOD (about 120 μg). This figure was used for the planning of the adsorption of EC-SOD from human tissue homogenates.

EXAMPLE 4

Immunoadsorption of EC-SOD to anti-EC-SOD-Sepharose®

About 10 l of umbilical cord extract prepared as described in Example 1 was handled at a time. The EC-SOD content of the extract was about 150 U/ml. If the gel binds 13,600 U/ml (cf. Example 3), adsorption of all EC-SOD in 10 l of extract required about 110 ml of anti-EC-SOD-Sepharose.

First the extract is centrifuged (6000×g, 30 min.) to remove precipitated protein. To the supernatant was then added 110 ml of anti-EC-SOD-Sepharose, and the mixture was incubated overnight at 4° C. with stirring. The gel was separated from the extract on a glass funnel. The gel was then washed on the funnel with large amounts of 50 mM K phosphate, pH 7.0+0.5M NaCl.

The gel was packed in a chromatography column with a diameter of 5 cm. The elution started with 50 mM K phosphate, pH 7.0+0.5M NaCl at a rate of 50 ml/hr and the absorbance at 280 nm is recorded. The elution was continued until a very low $A_{280}$ is attained. The EC-SOD was then eluted with a linear gradient of KSCN, 0.5–2.5M, in 50 mM K phosphate, pH 7.0. The total volume of the gradient is 500 ml, and the elution is run at 30 ml/hr. The desorption of EC-SOD was slow and the elution could not be speeded up.

The eluting fluid was collected in a fraction collector. To protect eluted EC-SOD from the high KSCN concentration, a T-pipe was inserted into the plastic tube from the eluting end of the column and distilled water injected at twice the rate of the column elution.

The resulting elution of protein (at $A_{280}$) and EC-SOD is shown in FIG. 1. It appears that the elution of EC-SOD is not complete at the end of the gradient 2.5M KSCN, but the elution is not continued in order not to collect EC-SOD which has become too denatured by the high KSCN-concentration.

The EC-SOD was pooled as shown in the figure. The first activity in the gradient were not collected since it contained a rather large amount of contaminating, unspecifically bound protein ($A_{280}$). Most of the $A_{280}$ in the gradient is contributed by the KSCN, and only in the beginning is a significant small protein peak seen. For regeneration the gel is then shaken overnight in the 2.5M KSN, then washed with 50 mM K phosphate, pH 6.5+0.5M NaCl and then with buffer without any NaCl. Azide is finally added as an antibacterial agent. Before use the gel is washed with azide-free 50 mM K phosphate pH 6.5.

EXAMPLE 5

Adsorption to and Elution from DEAE-Sephocel®

To the pooled eluate from the anti-EC-SOD-Sepharose column was added 1-aminomethylpropanol to a final concentration of 10 mM. The solution was then titrated to pH 9.0 with 1M NaOH. The solution was diluted with about 5 volumes of distilled water. To the resulting solution was added 40 ml DEAE-Sephacel® equilibrated with 50 mM Na phosphate +0.5M NaCl+175 mM Tris-HCl pH 9.6.

Figure 2:
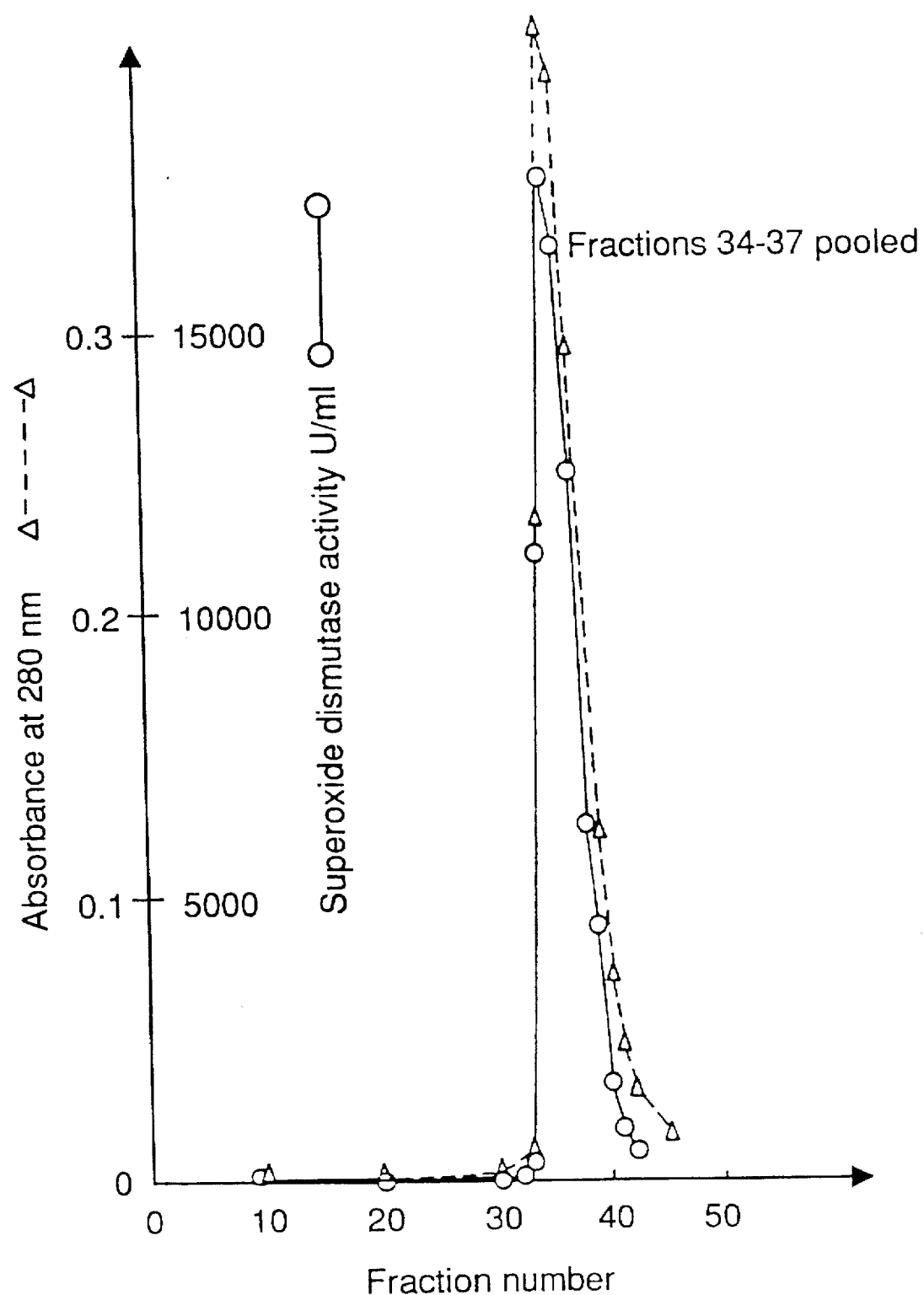
FIG. 2 is a graph showing the elution pattern of EC-SOD from DEAE-Sephacel® (cf. Example 5).

The EC-SOD was allowed to adsorb to the DEAE-Sephacel® with stirring overnight at 4° C. The DEAE-Sephacel® was then collected on a glass-funnel, washed with 50 mM Na phosphate, pH 6.5, and packed in a chromatography column with a diameter of 2.5 cm. The column was first eluted with about 4 volumes of the above buffer. The EC-SOD was then eluted with 50 mM Na phosphate pH 6.5+0.25M NaCl as shown in FIG. 2. The activity was pooled as shown in FIG. 2, dialyzed against 25 mM Na phosphate pH 6.5, and finally concentrated to about 2 ml.

EXAMPLE 6

Final Purification of EC-SOD on heparin-Sepharose®

Four batches of eluate from the DEAE-Sephacel®, as described above, were separated at a time on heparin-Sepharose®. The enzyme solutions to be applied were dialyzed against 25 mM K phosphate pH 6.5.

Figure 3:
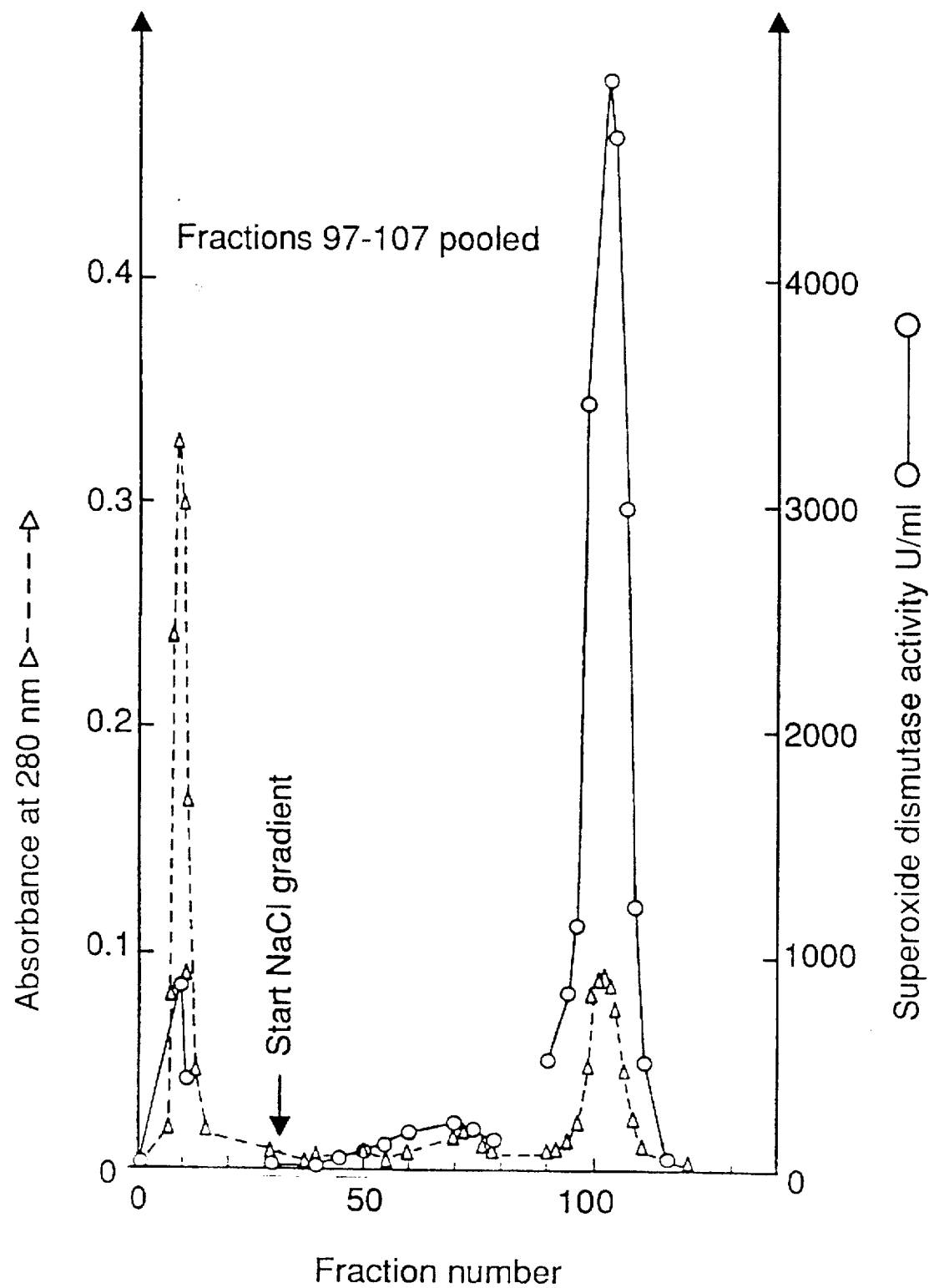
FIG. 3 is a graph showing the elution pattern of EC-SOD from heparin-Sepharose® (cf. Example 6).

20 ml heparin-Sepharose® gel was prepared as recommended by the manufacturer (Pharmacia, Uppsala, Sweden), and washed with 25 mM K phosphate pH 6.5 containing 1M NaCl and then with buffer without NaCl. The heparin-Sepharose® was packed in a chromatography column with a diameter of 2.5 cm, and elution was started with 25 mM K phosphate pH 6.5 at 15 ml/hr. The EC-SOD solution (about 10 ml, 800,000 units) was then applied and the absorbance at 280 nm monitored (cf. FIG. 3). When, after the first peak, the $A_{280}$ approached the base-line, the EC-SOD was eluted with an NaCl gradient from 0 to 1.2M NaCl. The gradient volume was 400 ml. The EC-SOD eluted in three peaks; one with no affinity for heparin, one with intermediate affinity and one with high affinity. The peaks correspond to the fractions A, B and C described in Example 2. When purified by the present procedure, almost all activity is of type C, and it was therefore concluded that this is likely to be the native form of the enzyme. Peak C was pooled as shown in FIG. 3.

The pooled activity was 430,000 units (about 4.3 mg). The specific activity was 81100 (U per ml/$A_{280}$). On SDS-PAGE gel subunits of about 30,000 D were found. No trace of contamination was seen. The pooled activity respresented about 53% of the activity applied on the heparin-Sepharose®.

EXAMPLE 7

The amino-terminal Sequence of Human EC-SOD

Human EC-SOD obtained as described in the preceding Examples was analysed for its (N-terminal) amino acid sequence by standard procedures (Edman et al., *Eur. J. Biochem.* 1, 1967, pp. 80–87). The sequence of the first 33 amino acids was found to be:

TRP THR GLY GLU ASP SER ALA GLU PRO ASN SER ASP SER ALA GLU TRP ILE ARG ASP MET TYR ALA LYS VAL THR GLU ILE TRP GLN GLU VAL MET GLN

This sequence—or a suitable part of it—may be employed to produce synthetic DNA probes, synthetic deoxyoligonucleotides complementary to both the coding and non-coding strand of the DNA sequence coding for the amino acid sequence shown above.

Such probes may be used in hybridization experiments with cDNA libraries produced from mRNA from EC-SOD-producing cells or tissues, in order to isolate a full-length or partial cDNA copy of an EC-SOD gene, as described in the following Example.

EXAMPLE 8

Cloning and Sequencing of Human EC-SOD
Preparation of a DNA Probe

Human EC-SOD was purified from umbilical cords substantially as described in Examples 1–6 above, and the sequence of the first 33 N-terminal amino acids was determined as described in Example 7. On the basis of this amino acid sequence and the postulated codon usage (Grantham et al., *Nucl. Acids Res.* 9, 1981, pp. 43–74) for eukaryotic proteins, a synthetic 48-meric deoxyoligonucleotide

5'-CAGGGACATGTATGCCAAGGTGACTGAGATCTGGCA

GGAGGTGATGCA-3' complementary to the coding strand of the EC-SOD gene was synthetized according to the procedure described by Matthes et al. (*EMBO Journal* 3, 1984, pp. 801–805).

Screening of a Human Placenta cDNA Library

A human placenta cDNA library prepared in the vector λgt11 was obtained from Clontech Laboratories, Inc., 922

Figure 4:
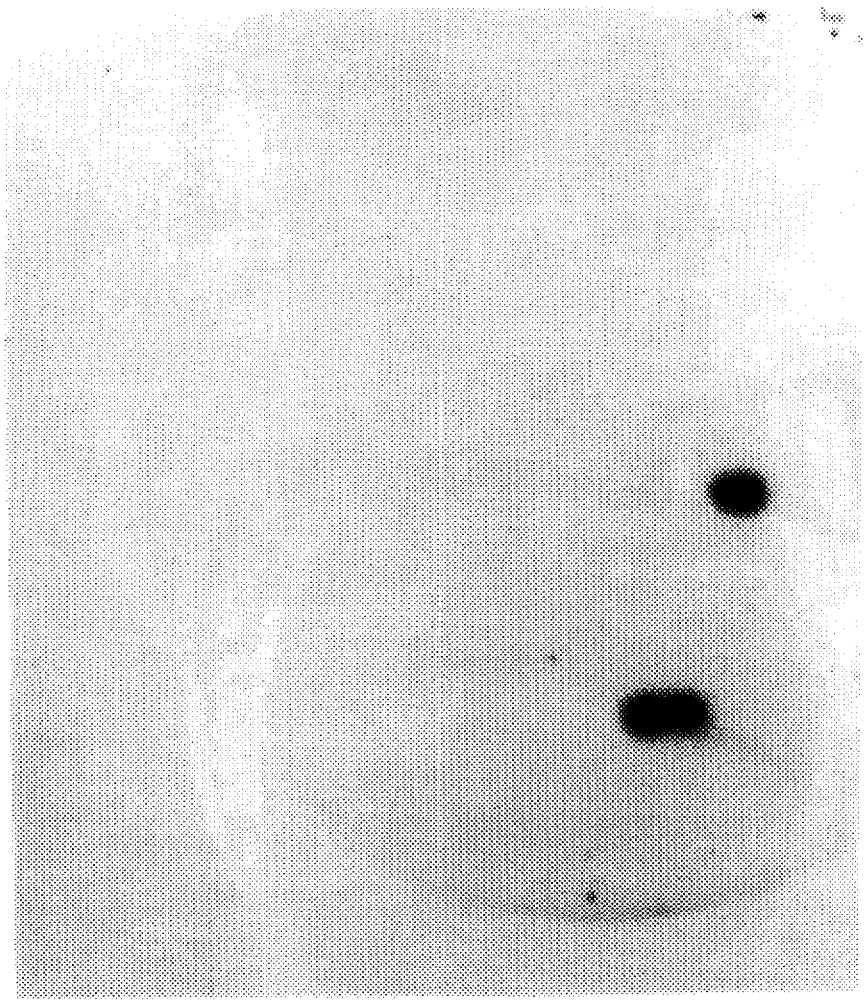
FIG. 4 is an autoradiogram showing the hybridization pattern with the 48-meric probe of one of the nitrocellulose filters onto which about 20,000 λgtll plaques had been transferred. The dark spots on the autoradiogram represent human EC-SOD-cDNA-containing plaques (cf. Example 8).

Industrial Avenue, Palo Alto, Calif. 94303, USA (Catalogue No. HL 1008 Lot No. 1205). The recombinant phages were screened for human EC-SOD cDNA sequences by plating the phages on the indicator strain *E. coli* Y 1090. Transfer of plaques to and treatment of nitrocellulose filters (Hybond C, Amersham Inc.) were essentially as described by Maniatis et al. (*Molecular Cloning, A Laboratory Manual*, Cold Spring Harbor Laboratories, 1982). Eight nitrocellulose filters to which 20,000 plaques had been transferred per filter, were presoaked in: 5×SSC and then prehybridized for one hour at 41° C. in 40 ml of 20% formamide, 5×Denhardt's solution, 50 mM sodium phosphate, pH 6.8, and 50 µg/ml of denatured sonicated calf thymus DNA. The filters were then hybridized to $7 \times 10^5$ counts per minute per ml of the $^{32}$P-γ-ATP end-labelled (cf. Maniatis et al., op.cit.) 48-meric probe described above. The hybridization was performed in the prehybridization solution supplemented with 100 µM ATP (final concentration) for 18 hours at 41° C. After incubation overnight at 41° C., the filters were washed once in 0.2×SSC at 37° C. followed by 4 washes in 0.2×SSC., 0.1% SDS, at 37° C. and were then allowed to air-dry. The filters were exposed to DuPont Cronex 4 X-ray film overnight. FIG. 4 shows one of the autoradiograms. Each filter contained about 6 positive plaques.

Phages from plaques showing a positive hybridization reaction were isolated and purified, and DNA from these phages was extracted by the methods described by Davis et al. (*Advanced Bacterial Genetics*, Cold Spring Harbor Laboratories, 1980), and the length of the cDNA inserts was determined by agarose gel electrophoresis after cleavage of the phage DNA with the restriction endonuclease EcoRI. The recombinant phage carrying the longest cDNA insert was designated λSP3 and was chosen for further studies.

The cDNA insert from phage λSP3 was subjected to restriction endonuclease analysis and sequenced after subcloning into pUC18 and the M13 vector mp9, respectively. The insert was demonstrated to be DNA encoding human EC-SOD by comparing the amino acid sequence derived from the DNA sequence with the peptide sequence of the purified protein and by its expression product in CHO cells. The insert isolated from λSP3 contained 1396 bp of cDNA and an open reading frame encoding a protein of 240 amino acids and a 69 bp 5' untranslated region and a 607 bp 3' untranslated region. (See FIGS. 5A and B)

Subcloning and Restriction Endonuclease Analysis of cDNA Inserts Encoding Human EC-SOD About 30 µg of λSP3 DNA were digested with the restriction endonuclease EcoRI, and the cDNA insert was separated from λ DNA by electrophoresis in a 6% polyacrylamide gel. Approximately 0.2 µg of the cDNA fragment was isolated from the gel by electroelution, phenol and chloroform extraction and ethanol precipitation (Maniatis et al., supra). 0.05 µg of the isolated cDNA fragment was ligated to 1 µg of restriction endonuclease EcoRI-digested alkaline phosphatase treated pUC18 DNA (Norrander et al., *Gene* 26, 1983, pp. 101–106). The ligated DNA was transformed to strain *E. coli* HB101 (*J. Mol. Biol.* 41, p. 459). Transformants were selected on plates containing ampicillin. A recombinant plasmid carrying the cDNA insert was identified and designated pLS3. Plasmid pLS3 DNA was subjected to restriction endonuclease analysis.

DNA Sequence Analysis of cDNA Encoding Human EC-SOD

The DNA sequence of the cDNA insert from phage λSP3 encoding human EC-SOD was determined by the procedures of Sanger et al. (*Proc. Natl. Acad. Sci. USA* 74, 1977, pp. 5463–5467; F. Sanger and A.R. Coulson, *FEBS Letters* 87, 1978, pp. 107–110) and Messing et al. (*Nucl. Acids Res.* 9, 1981, pp. 309–321; P. H. Schreir and R. Cortese, *J. Mol. Biol.* 129, 1979, pp. 200–172) after cloning of the cDNA fragment into EcoRI site the M13 vector mp9 (J. Messing and J. Vieira, *Gene* 19, 1982, pp. 269–276).

A sequential series of overlapping clones of the cDNA insert was generated in the M13 vector mp9 according to the method described by Dale et al. (*Plasmid* 13, 1985, pp. 31–40). Using this method the complete nucleotide sequence of both DNA strands of the cDNA was determined and was found to have a length of 1396 bp.

The nucleotide sequence and deduced amino acid sequences of the cDNA insert of λXPS3 are shown in FIG. 5. The cDNA insert has an open reading frame of 240 amino acids. The amino acid sequence of the purified mature protein is initiated at amino acid +1 which suggests a putative signal peptide of 18 amino acids. Like known signal peptides, this sequence of amino acids is rich in hydrophobic amino acids and moreover, the last residue is alanin which is one of the amino acids found in this position in known signal peptides (G. Von Heijne, *Eur. J. Biochem.* 133, 1983, pp. 17–21). Underlined amino acid sequences have been confirmed by peptide sequencing.

Another feature of the DNA sequence is the sequence found at the translation initiation codon, -CAGCCAUGC-, which is homologous to the postulated consensus sequence for eukaryotic initiation sites, -CC$_G^A$CC-AUG(G)- (M. Kozak, *Nucl. Acids Res.* 12, 1984, pp. 857–872). Moreover, a possible polyadenylation signal with the sequence -ATTAAA- homologous to the postulated consensus sequence AATAAA is found 14 bp upstream of the polyadenylation tail.

Expression of Human EC-SOD in CHO Cells

Figure 6:
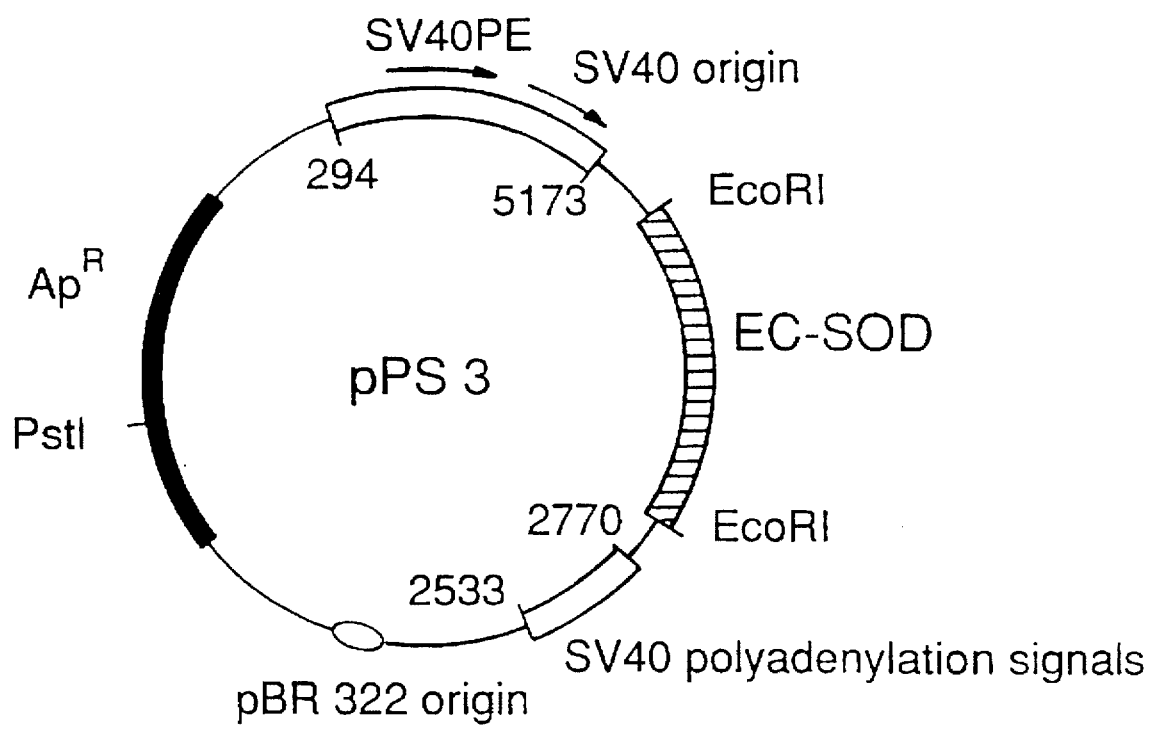
FIG. 6 shows the structure of plasmid pPS3. The white areas represent SV40 DNA and the numbers refer to the corresponding nucleotide positions in SV40. SV40PE and SV40 origin represent the SV40 early promotor and the SV40 origin of replication, respectively, and arrows show the direction of transcription and DNA replication, respectively. SV40 polyadenylation signals are located between positions 2770 and 2533. The hatched area represents human EC-SOD cDNA. The solid black area represents the β-lactamase gene ($AP^R$) of plasmid pBR322. Thin lines represent plasmid pBR322 DNA. Also indicated is the location of the pBR322 origin of replication.

An expression vector containing the Simian Virus 40 (SV40) origin of replication, early and late promoters, polyadenylation and termination sequences was used to produce human EC-SOD encoded by the cDNA described above. The 1396 bp long cDNA was inserted into a unique EcoRI restriction endonuclease cleavage site located between the SV40 early promoter and the SV40 polyadenylation and termination sequences so that the expression of the coding sequence for human EC-SOD is controlled by the SV40 early promoter (FIG. 6). This constructed EC-SOD expression plasmid was designated pPS3.

20 µg of pPS3 DNA were linearized by cleavage with the restriction endonuclease PstI at the unique PstI site located in the β-lactamase gene. The linearized pPS3 DNA was co-transfected with 0.5 µg of DNA from a plasmid containing sequences conferring resistance to Geniticin (G-418 sulphate, Gibco Ltd.) into CHO-K1 (ATCC CCL61) cells by the method of Graham and Van der Eb (*Virology* 52, 1973, pp. 456–467). Transfected cells were selected by growth in medium (Hams's F12 medium supplemented with 10% fetal calf serum, streptomycin and penicillin) containing 700 µg per ml of Geniticin (G-418 sulphate, Gibco Ltd.). Geniticin resistant colonies were isolated and propagated in the same medium. Medium was removed at intervals and assayed for the presence of EC-SOD by ELISA and enzyme activity measurements as described below.

Several of the cell lines tested showed comparable production of human EC-SOD and one of the obtained cell lines was denoted CHO-K1/pPS3neo-18 and selected for further studies.

Secretion of EC-SOD into the Culture Medium by CHO Cells Containing the Gene Encoding Human EC-SOD The clone CHO-K1/pPS3neo-18 and the parental CHO-K1cells were grown to confluency in Ham's F-12 medium containing 10% of fetal calf serum. After 3 additional days the medium was removed and the cells washed twice with phosphate buffered saline. The cells were then detached from the culture flasks by means of incubation in a solution containing 40 mM Tris-HCl, 140 mM NaCl and 1 mM EDTA. The recovered cells (about $8\times10^6$) were then centrifuged, the supernatant discarded and the cells stored at $-80°$ C. as a pellet. The cells were then disintegrated with sonication in 1.5 ml of a solution containing 50 mM K phosphate pH 7.4, 0.3M KBr, 3 mM DTPA, 0.5 mM PMSF and 100 KIE/ml trasylol. The homogenates were centrifuged. Specific determination of the amount of EC-SOD was performed by means of incubation of the homogenates and culture media with immobilized antibodies directed towards human EC-SOD and human CuZn SOD, as outlined in Öhman and Marklund, Chim. Sci. 70, 1986, pp. 365–369. No EC-SOD was found in the parental CHO K1 cells or in their culture medium. The culture medium from the clone CHO-K1(pPS3neo-18 (15 ml) cells was found in this particular experiment to contain 51 U/ml EC-SOD, total 765 U. The cell homogenate (in 1.5 ml) contain 71 U of SOD activity of which 20 U was human EC-SOD. Thus, 97.5% of the EC-SOD in the CHO-K1/pPS3neo-18 culture was secreted into the medium.

Production of Human EC-SOD in CHO Cells

The production of human EC-SOD by this clone was determined both when the cells were grown on a solid support and in suspension.

1. Production of EC-SOD by CHO-K1/pPS3neo-18' Cells Growing on Solid Supports a) A 175 cm$^3$ flask was inoculated with $4.5\times10^6$ cells in 30 ml of Ham's F12 medium (Flow Laboratories) supplemented with 10% fetal calf serum, 2 mM L-glutamine, streptomycin and penicillin. The cells were incubated at 37° C. in air containing 5% $CO_2$. Medium was changed every third day, and the concentration of human EC-SOD secreted into the growth medium was determined as described below in the section entitled "Assays for detection of the expression of human EC-SOD". The productivity of human EC-SOD was 1.5 pg·cell$^{-1}$·24 hours$^{-1}$ as measured by ELISA and by determining the EC-SOD enzyme activity.

b) Microcarriers (m.c) (Cytodex 3, Pharmacia, Sweden), 4 mg/ml, were inoculated with cells at a concentration of 7 cells/m.c in Ham's F12 medium (Flow Laboratories) supplemented with 5% fetal calf serum, 2 mM L-glutamine, streptomycin and penicillin.

The cells were grown in a 500 ml stirrer flask (Techne) at 37° C. in 5% $CO_2$ in air. At confluent cell growth, the culture was perfundated at a rate of 0.088·h$^{-1}$.

The productivity of human EC-SOD was 0.50 pg·cell$^{-1}$·24 hours$^{-1}$.

2. Production of EC-SOD by CHO-K1/pPS3neo-18 cells grown in suspension culture 125 ml of medium (Ham's F12 supplemented with 10% fetal calf serum, 2 mM L-glutamine, streptomycin and penicillin) were inoculated to $2\times10^5$ cells/ml. The culture was incubated in spinner flasks (Techne) at 37° C. in air containing 5% $CO_2$.

Every third day medium was changed. Productivity of human EC-SOD was 0.65 pg·cell$^{-1}$·24 hours$^{-1}$.

Assays for the Detection of Expression of Human EC-SOD

1. Enzyme linked immunoadsorbent assay (ELISA)

Microtiter plates (Nunclon, NUNC A/S, Denmark) were coated with 100 µl per well of a solution containing 15 µg per ml of polyclonal rabbit anti-EC-SOD IgG antibodies (prepared as described in Example 3) in 15 mM $Na_2CO_3$, 35 mM $NaHCO_3$, 0.02% $NaN_3$, pH 9.6. After incubation overnight at room temperature, the plates were washed with PBS (10 mM sodium phosphate, 145 mM NaCl, pH 7.2). The microtiter plates were incubated for 30 minutes at 37° C. with 200 µl per well of a solution containing 3% (w/v) bovine serum albumin in PBS and washed with PBS. 100 µl of diluted medium samples were added to each well and incubated for 1 hour at 37° C. The plates were washed with 5% Tween® 20 (v/v) in PBS followed by incubation for 1 hour at 37° C. with 100 µl per well of a solution containing 8 µg per ml of a mouse monoclonal anti-EC-SOD antibody (see Example Z) in 3% bovine serum albumin in PBS. After washing with 5% Tween® 20 in PBS, the plates were incubated for 1 hour at 37° C. with a peroxidase-conjugated rabbit anti-mouse antibody (Dakopatts A/S, Denmark) in 3% bovine serum albumin in PBS. The plates were washed with 5% Tween® 20 in PBS and incubated for 20 minutes at room temperature in the dark with 100 µl per well of a substrate solution (50 mM sodium citrate, 100 mM sodium phosphate, 0.04% (w/v) o-phenylene diamine, 0.01% $H_2O_2$, pH 5.0). The reaction was stopped by adding 25 µl of 10% SDS per well and the absorbance at 450 nm measured.

2. Determination of EC-SOD enzyme activity

SOD enzyme activity was determined as described in Marklund, J. Biol. Chem. 251, 1976, pp. 7504–7507. To achieve specificity for human EC-SOD the samples were analysed before and after treatment with anti-human EC-SOD immobilized on Sepharose® (see Example 4). EC-SOD activity was taken as the difference between the activity of the sample before and after adsorption to the antibody.

EXAMPLE 9

Heparin-Induced Release of EC-SOD into Human Blood Plasma

Figure 7:
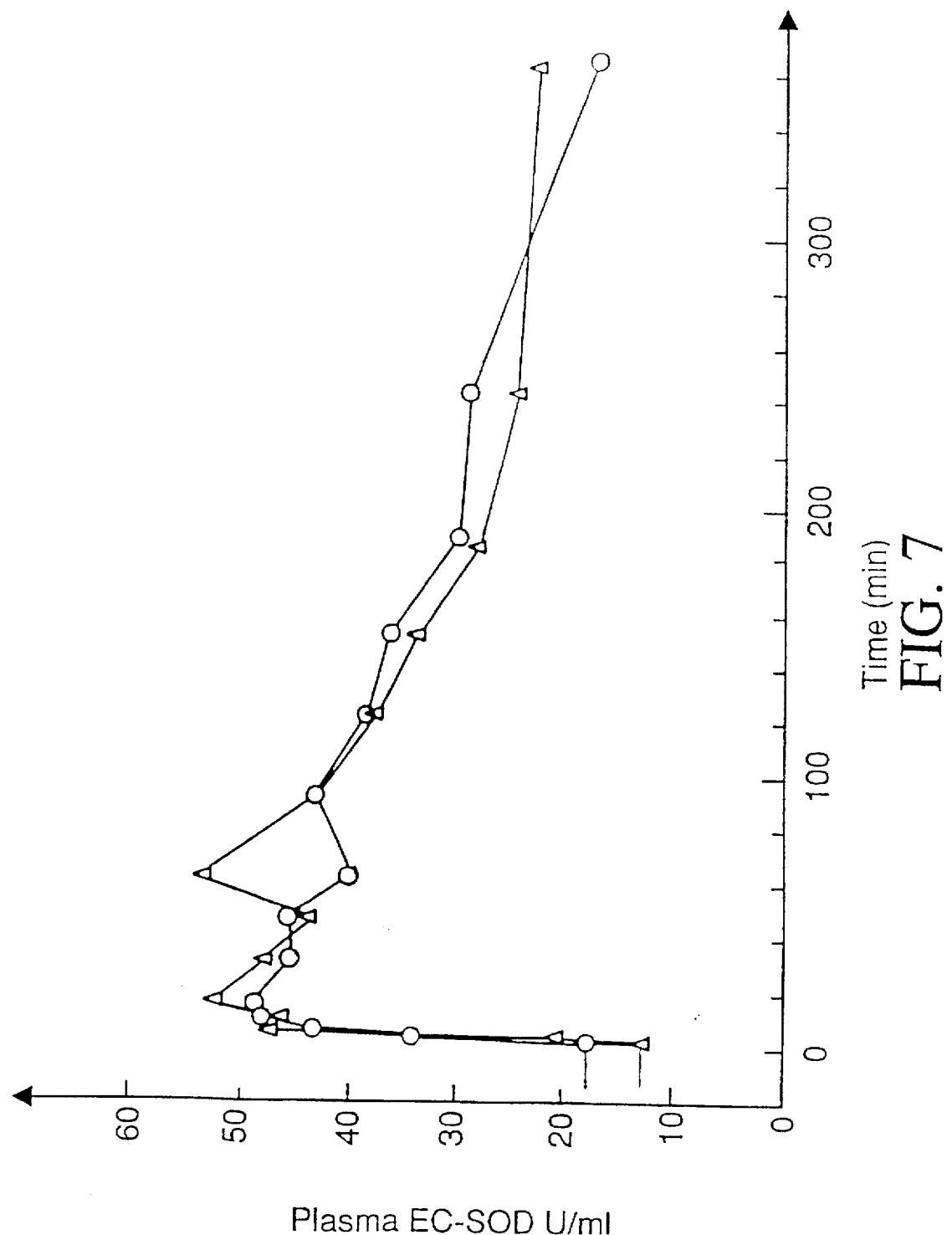
FIG. 7 shows the effect of intravenous heparin injection on plasma EC-SOD. 200 IU heparin per kg body weight was injected at time zero into two healthy males and plasma collected before and at indicated times after. The EC-SOD activity was determined as described in Example 9.

200 IU/kg body weight of heparin (obtained from AB KABI-Vitrum, Stockholm, Sweden) were injected intravenously into two healthy males fasted overnight [a) 34 years of age and b) 40 years of age]. Blood samples were taken before heparin injection and at intervals after the injection as indicated in FIG. 7. The blood samples were tapped into Terumo Venoject vacuum tubes containing EDTA as anticoagulant and centrifuged. After centrifugation, the plasma samples were kept at $-80°$ C. until assay.

Furthermore, 20 ml of whole blood were taken from three healthy persons and kept in EDTA tubes as described above. The blood was divided into two equal parts and to one was added 30 IU heparin/ml and to the other an equal volume of 0.15M NaCl. After incubation for 30 minutes at room temperature, the samples were centrifuged and the plasma collected for SOD assay.

SOD activity was assayed by means of the direct spectrophotometric method employing $KO_2$ (S. L. Marklund, J. Biol. Chem. 251, 1976, pp. 7504–7507) with modifications as described in "Öhmann and Marklund, Clin. Sci. 70, 1986, pp. 365–369. One unit of SOD activity corresponds to 8.3 ng human CuZnSOD, 8.8 ng human EC-SOD and 65 ng bovine MnSOD. Distinction between isoenzymes in plasma was achieved by means of antibodies towards human CuZnSOD and EC-SOD immobilized on Sepharose® 4B as described in Öhmann and Marklund, Clin. Sci. 70, 1986, pp. 365–369.

The results are shown in FIG. 7 indicating that an intravenous injection of 200 IU heparin per kg body weight leads to a rapid three-fold rise in plasma EC-SOD activity. The maximum increase is approached already after 5 minutes. The activity stays high for 15–30 minutes and then decreases gradually to approach the initial level after more than 6 hours. Intravenously injected heparin had no effect on the plasma CuZnSOD and cyanide resistant SOD activities.

Figure 8:
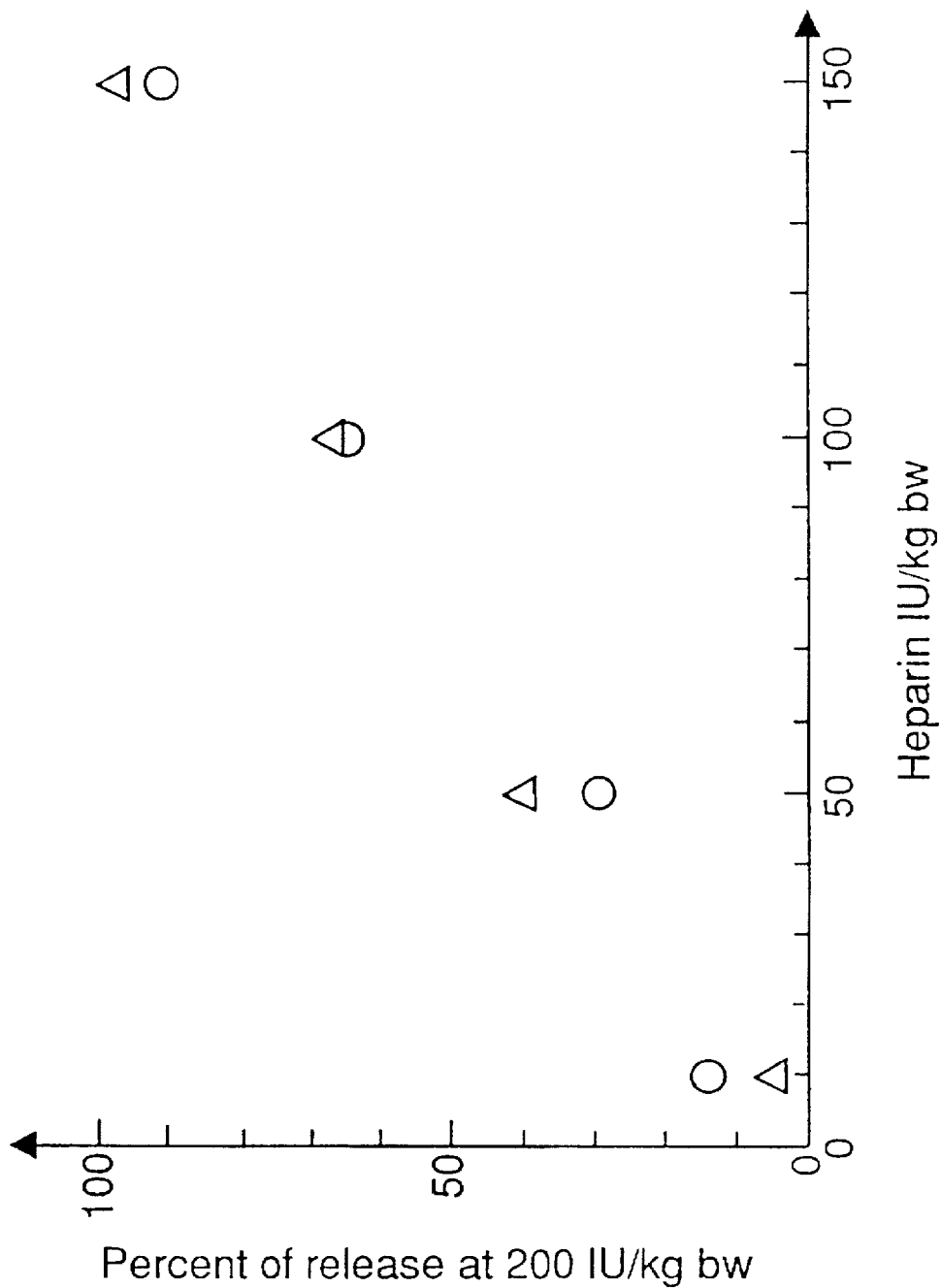
FIG. 8 shows the dose response of the EC-SOD releasing activity of intravenous heparin. Heparin was injected intravenously at the indicated doses into two healthy males and blood was collected before and at 10 and 15 minutes after the heparin injection. At 15 minutes an additional dose of heparin up to 200 IU/kg body weight, was injected and blood collected 10 minutes thereafter. EC-SOD was determined in plasma as described in Example 9. The difference between the preheparin EC-SOD activity and the activity after the second heparin injection was taken as 100% release. The difference between the preheparin activity and the mean activity of the 10 and minutes samples after the first dose are presented in relation to the "100% release". The separate experiments were performed with intervals of at least 4days (cf. Example 9).

The effect of administering up to 200 IU/kg body weight of intravenous heparin on the release of EC-SOD to plasma is shown in FIG. 8. It appears from the figures that increasing doses of heparin result in an increased release of EC-SOD. Apparently no distinct plateau is reached and it is likely that doses over 200 IU/kg body weight would result in an even higher EC-SOD release. Ethical considerations, however, precluded testing of higher doses.

Contrary to the results obtained in vivo, addition of heparin to whole blood as described had no effect on the plasma EC-SOD activity. Nor did addition of heparin (5 IU/ml) directly to plasma result in any change in the EC-SOD activity. The results indicate that the increase in plasma EC-SOD activity in vivo as seen in FIG. 7 is not caused by any release of the enzyme from blood cells, or by activation of the EC-SOD present in plasma.

Plasma samples from 5 healthy persons (3 males, 2 females) were subjected to chromatography on heparin-Sepharose® (purchased from Pharmacia, Uppsala, Sweden). Chromatography was carried out at room temperature in columns containing 2 ml of heparin-Sepharose® with 25 mM potassium phosphate, pH 6.5, as eluant. The samples (2 ml plasma) were applied at 4.2 ml/h and when the $A_{280}$ approached baseline, bound components were eluted with a linear NaCl gradient in the potassium phosphate buffer (0–1M, total volume 50 ml) at 9 ml/h (cf. FIG. 9). The mean yield of SOD activity in the eluate was about 95%.

Before application, the plasma samples were equilibrated with the elution buffer by means of chromatography on small Sephadex® G 15 columns (PD-10) (also purchased from Pharmacia, Uppsala, Sweden). The chromatography resulted in a three-fold dilution of the samples. The recovery of SOD activity was close to 100%.

Figure 9:
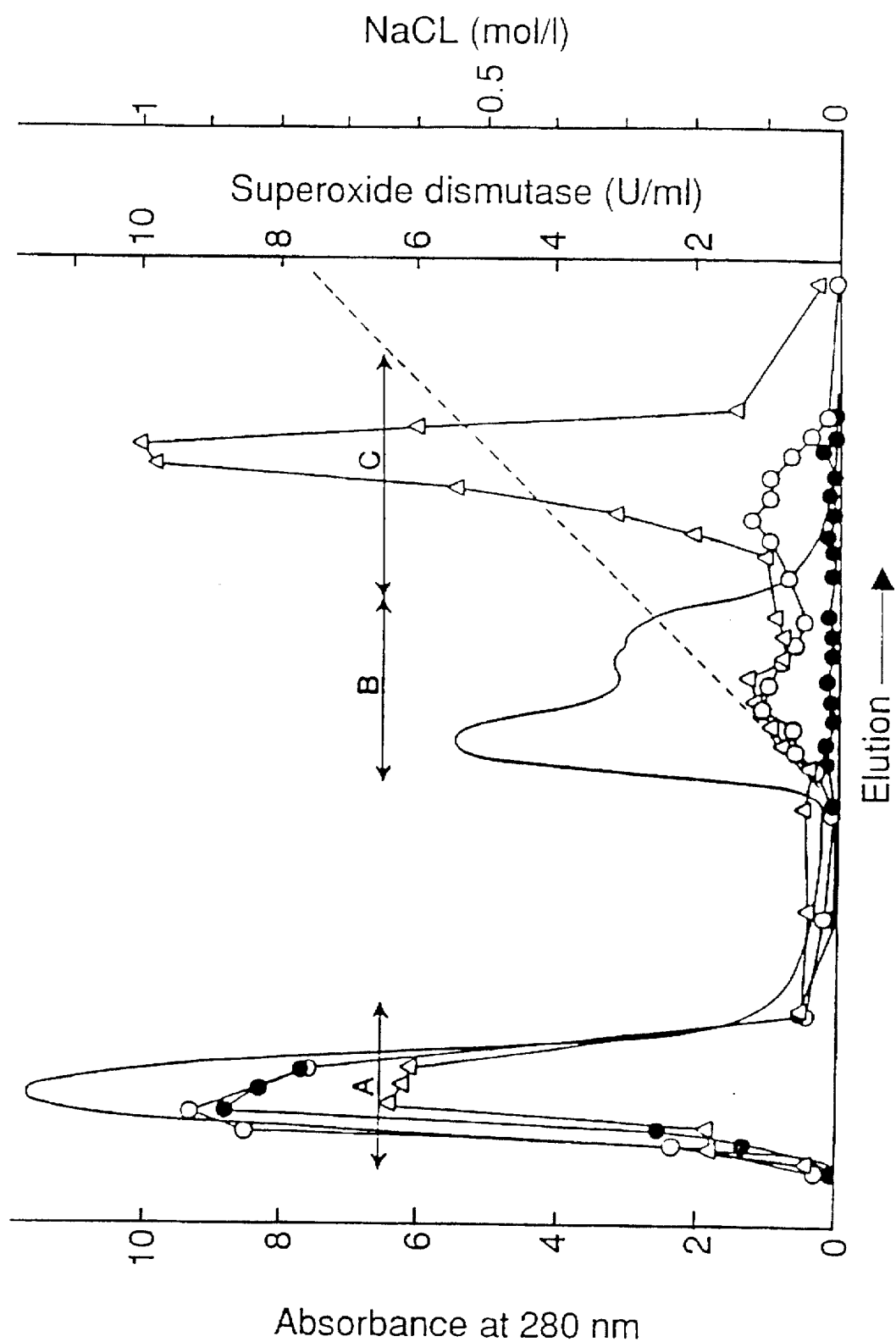
FIG. 9 shows the separation of plasma on heparin-Sepharose®. Human plasma collected before (○) and 10 minutes after intravenous injection of heparin (200 IU/kg body weight) (△) was separated on heparin-Sepharose® as described in Example 9. (●) indicates the result of chromatography of the preheparin plasma sample after pretreatment with anti-EC-SOD-Sepharose® to remove EC-SOD. The full line represents absorbance at 280 nm and the dotted line the NaCl gadient. EC-SOD fractions A, B and C were determined in pools as indicated in the figure. The activity in pool B and C represents EC-SOD only, since all activity was adsorbed by the anti-EC-SOD-Sepharose®. Pool A contains also CuZn SOD and cyanide resistant SOD activity. The EC-SOD activity in fraction A was therefore determined with immobilized antibodies as described for plasma in Example 9. The EC-SOD fractions A, B and C were 5.2, 4.4 and 5.1 U/ml in preheparin plasma and 7.7, 5.7 and 29.4 U/ml in postheparin plasma. The recoveries of EC-SOD activity in the chromatograms were 84% and 83%, respectively. Note that the larger total SOD activity in pool A in the preheparin plasma chromatogram is due to hemolysis in the sample with release of CuZn SOD from erythrocytes (cf. Example 9).

The results of the determination of EC-SOD fractions A, B and C in five normal plasma specimens are shown in Table I below. It was found that the three fractions are roughly equally large in normal plasma. The mean yield of EC-SOD activity in the chromatogram was 95%. The separation into three fractions is apparently not caused by secondary in vitro degradation, since the patterns for a plasma specimen was identical before and after storage for 3 days in a refrigerator. The effect of intravenous heparin on the composition of EC-SOD fractions in plasma is shown in FIG. 9. It was found that intravenous injection of heparin in the person analysed leads to a significant increase in fraction C only. A and B remain essentially unchanged. In a second analysed person (data not shown), the effect of heparin injection was essentially identical. Fraction C increased from 7 to 32 units/ml plasma.

TABLE I

Separation of plasma EC-SOD into fractions A, B and C

| | EC-SOD; U/ml plasma Fractions | | |
|---|---|---|---|
| Age/sex | A | B | C |
| 40/male | 5.9 | 6.2 | 7.0 |
| 34/male | 5.2 | 4.4 | 5.1 |
| 32/male | 2.3 | 5.2 | 6.4 |
| 33/female | 2.3 | 5.9 | 8.3 |
| 29/female | 3.3 | 6.1 | 7.3 |
| mean ± SD | 3.5 ± 1.5 | 5.6 ± 0.8 | 6.8 ± 1.2 |

The experiments described above show that intravenous injection of heparin leads to a prompt increase in plasma EC-SOD activity. Heparin does not activate EC-SOD, nor can any release from blood cells be demonstrated, pointing to the endothelial cell surfaces as the most likely source of the released EC-SOD. A number of other factors with affinity for heparin, lipoprotein lipase, hepatic lipase, diamine oxidase, and platelet factor 4 have previously similarly been shown to be rapidly released by intravenous heparin. In most of these cases, there is evidence that heparin-induced displacement of the protein from heparan sulfate on endothelial cell surfaces is the explanation of the phenomenon (A. Robinson-White et al., *J. Clin. Invest.* 76, 1985, pp. 93–100; C. Busch et al., *Throm. Res.* 19, 1980, pp. 129–137). It is likely that the release of EC-SOD can be explained in the same way.

No distinct plateau in the release was reached for heparin doses up to 200 IU/kg body weight, showing that more heparin is needed for maximum release of EC-SOD than for lipoprotein lipase, diamine oxidase, hepatic lipase, and platelet factor 4. The ratio between the affinity for heparin and heparan sulfate might be lower for EC-SOD than for the other proteins.

Basal human plasma contains nearly equal amounts of EC-SOD fraction A, B and C. Intravenous heparin released only the high-heparin affinity fraction C., which is apparently the form which has affinity for endothelial cell surfaces. The increase achieved here was 4-6-fold, but it is likely that higher doses of heparin would result in a higher ratio. Much higher ratios are achieved for lipoprotein lipase, hepatic lipase, diamine oxidase, and platelet factor 4. Compared with these proteins, the endothelial binding of EC-SOD appears rather loose. Possibly an equilibrium exists for EC-SOD fraction C between plasma and endothelial cell surfaces. Most EC-SOD in the vascular system appears to be located on the endothelial cell surfaces.

The molecular background for the difference in heparin affinity between EC-SOD fraction A, B and C is still unresolved. The amino acid and subunit compositions were not significantly different (S. L. Marklund, *Proc. Natl. Acad. Sci. USA* 79, 1982, pp. 7634–7638). Nor could any antigenic differences be detected (S. L. Marklund, *Biochem. J.* 220, 1984, pp. 269–272). The binding to negatively charged heparin is apparently not of a general ion-exchange nature since no difference between fraction A and C can be detected upon ion exchange chromatography, and their isoelectric points are identical (pH 4.5). The difference is not due to in vitro degradation, since storage of plasma for 3 days in a refrigerator did not change the elution pattern on heparin-Sepharose®. Although in vivo degradation is a possibility, one might speculate that fractions A and B are specifically intended for protection of fluid components and fraction C for shielding cellular surfaces.

Most cell types in the body possess heparan sulfate and other sulfated glucoseaminoglycanes on their surfaces (M. H ook et al., *Ann. Rev. Biochem.* 53, 1984, pp. 847–869). It is possible that much of the EC-SOD found in tissues (S. L Marklund, *J. Clin. Invest.* 74, 1984, pp. 1398–1403) is located on such substances on cell membranes and in the connective tissue. The binding of EC-SOD to cellular surfaces might be an especially efficient way of protecting cells against extracellularly formed superoxide radicals. It is interesting to note that substitution of CuZnSOD with polylysine to facilitate association with negatively charged cell membranes highly potentiated the ability of the enzyme to protect activated polymorphonuclear leukocytes against self-inactivation (M. L. Salin and J. M. McCord, in *Superoxide and Superoxide Dismutoses*, eds. A. M. Michelson, J. M. McCord and I. Fridovich, Academic Press, 1977, pp.

257–270). The cell membrane-associated SOD of *Nocardia asteroides* confers efficient protection to the bacterium against activated polymorphonuclear leukocytes (B. L. Beaman et al., *Infect. Immun.* 47, 1985, pp. 135–140). Microorganisms lacking affinity for EC-SOD fraction C would, unlike most cells in the body, not benefit from protection by the enzyme.

There is evidence that superoxide radicals produced by activated leukocytes and also by other cell types under certain conditions can, directly or indirectly, induce chromosomal damage (J. Emerit. *Lymphokines* 8, 1983, pp. 413–424; A. B. Weitberg, S. A. Weitzman, E. P. Clark and T. P. Stossel, *J. Clin. Invest.* 75, 1985, pp. 1835–1841; H. C. Birnboim and M. Kanabus-Kaminska, *Proc. Natl. Acad. Sci. USA* 82, 1985, pp. 6820–6824) and promote carcinogenesis (C. Borek and W. Troll, *Proc. Natl. Acad. Sci. USA* 8, 1983, pp. 1304–1307; Y. Nakamura, N. H. Colburn and T. D. Gindhart, *Carcinogenesis* 6, 1985, pp. 229–235). The surface-associated EC-SOD fraction C would be an efficient protector against such events in vivo. In most in vitro test systems, much of the EC-SOD fraction C would probably be lost from the cells since the binding appears to be weak. Findings in such systems are then not necessarily quantitatively predictive for the in vivo protection against damage.

Parenteral CuZnSOD has been shown to possess many interesting therapeutic properties as indicated above. The present findings suggest that administration of EC-SOD may be an even more efficient mode of protection against cellular damage caused by superoxide radicals in extracellular space.

EXAMPLE 10

Injection of $^{125}$I-labelled Human EC-SOD into Rabbits

Umbilical cord EC-SOD prepared as described in Examples 1 and 4–6 was labelled with $^{125}$I using the "Iodogen" technique (P. R. P. Salacinski, C. McLean, J. E. C. Sykes, U. V. Clement-Jones and P. J. Lowry, *Anal. Biochem.* 117, 1981, pp. 136–146). The labelled EC-SOD was separated from $^{125}$I-iodide by means of gel filtration on Sephacryl® S-300 (obtained from Pharmacia, Uppsala, Sweden). The location on the chromatogram was at the same site as unlabeled EC-SOD, which indicates that the molecular size had not changed.

The resulting labelled EC-SOD was chromatographed on heparin-Sepharose® (as described above). Only material with high heparin affinity (=fraction C) was used for further experiments.

The labelled EC-SOD was injected intraveneously into rabbits (weighing about 3 kg). Blood samples were then taken to analyse the radioactivity remaining in the plasma. The plasma samples were precipitated with trichloroacetic acid (which precipitates proteins) and the radioactivity was counted on the protein pellets after centrifugation. This eliminates counting of radioactive iodide and iodine-containing amino acids in the plasma, derived from degraded EC-SOD. The rabbits were given iodide in their drinking water to prevent relabelling with $^{125}$I of proteins in vivo.

After different times, heparin (2500 IU) was injected intraveneously into the rabbits, to study the effect of heparin. The results are shown in FIG. 10 and FIG. 11. 100% corresponds to the radioactivity that the plasma should theoretically contain, given the amount injected, and assuming that the total plasma volume in the rabbits were 5% of their body weight (e.g. 3 kg rabbit—150 ml of plasma).

Figure 10:
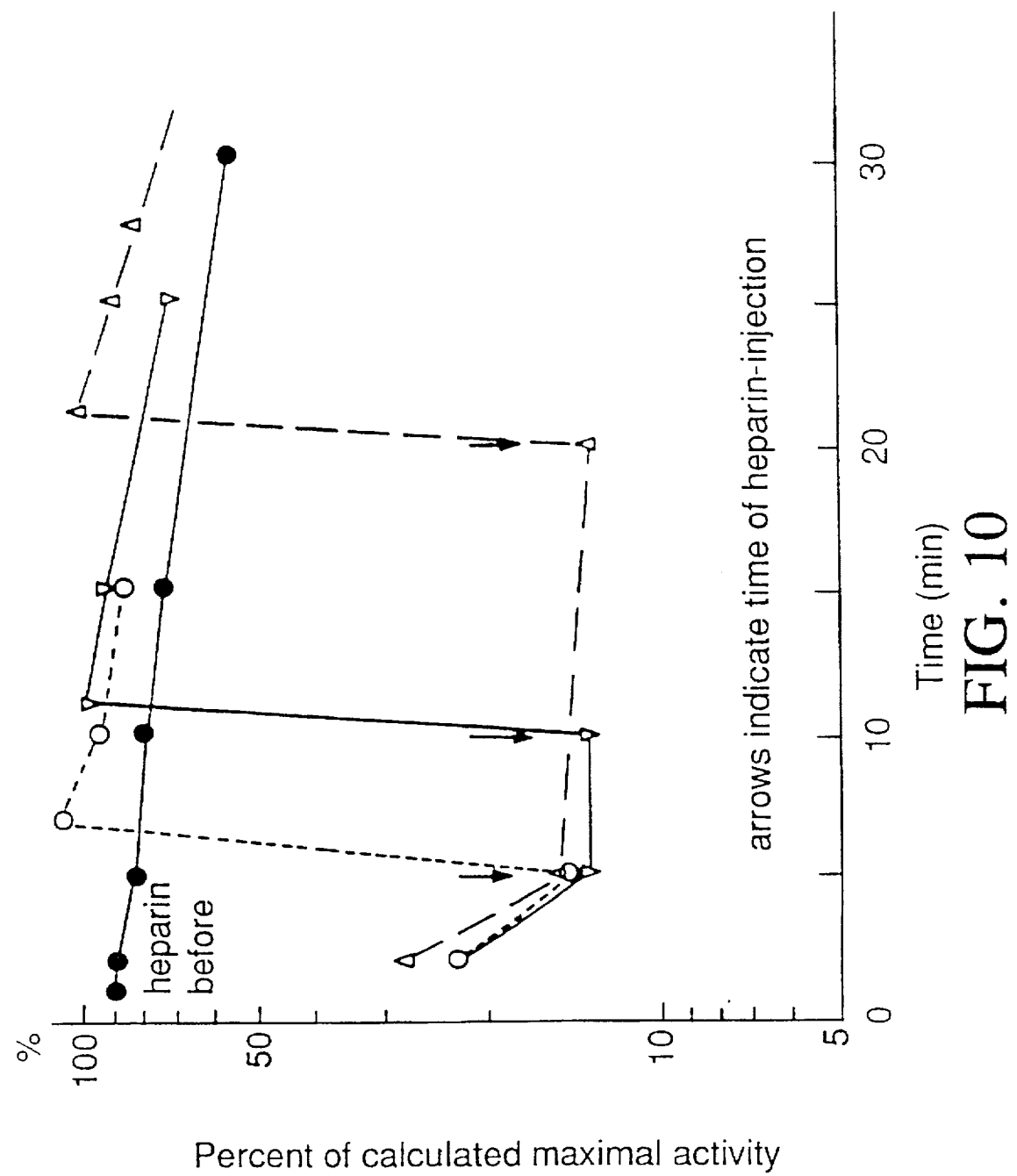
FIGS. 10 and 11 are graphs showing the effect of injection of $^{125}$I-labelled human EC-SOD into rabbits, and the effect of heparin injection (cf. Example 10).

FIG. 10 shows the results when heparin is injected before, and 2, 5, 10 and 20 minutes after $^{125}$I-EC-SOD.

After injection of labelled EC-SOD, a rapid decline in activity occurs within 5–10 minutes to about 15% of the theoretical maximum. When heparin is injected before EC-SOD, almost all the EC-SOD activity remains, with only a slow decline. When heparin is injected 2, 5, 10 and 20 minutes after the $^{125}$I-EC-SOD, there is a rapid increase in radioactivity and the peak reaches the theoretical maximum.

Figure 11:
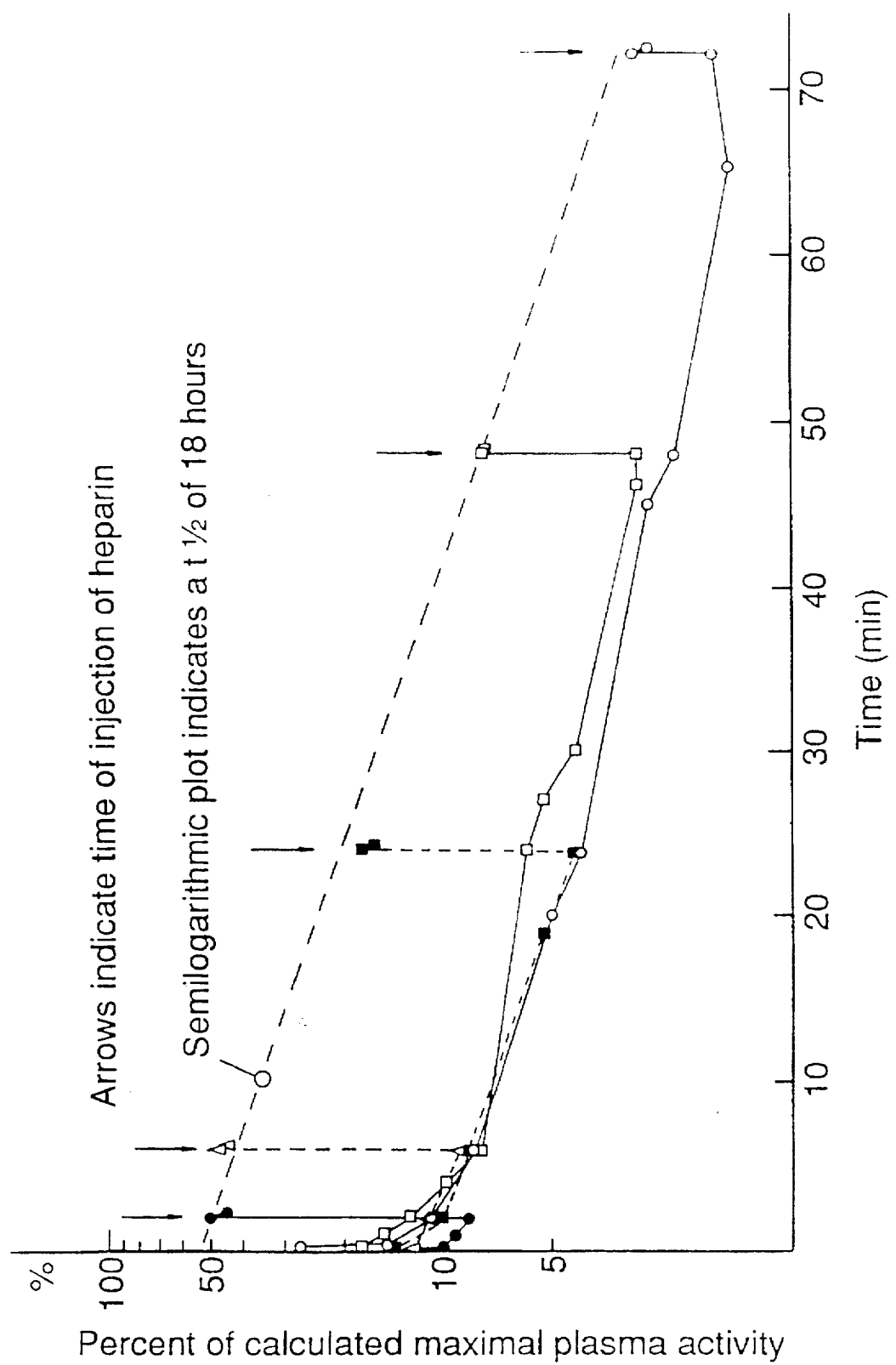

FIG. 11 shows injection of heparin after 2 hours to 72 hours. It appears from the figure that there is a rapid increase in activity, which, after 2 hours, reaches about 50% of the theoretical maximum and after 72 hours still reaches 3%.

There appears to be a rather rapid decline to 50% (at 2 hours), but after that the EC-SOD is eliminated far more slowly. Using the maxima in FIG. 11, a half-life (t ½) of about 18 hours can be calculated. It is probably longer in man, as turnover in the body of almost all components is faster in small animals.

The rapid increase in plasma EC-SOD (maximum reached within 2 minutes) after i.v. heparin indicates that the released $^{125}$I-EC-SOD was localized on the blood vessel endothelium which points to the same conclusion as in Example 8.

EXAMPLE 11

Binding of Human EC-SOD C to Pig Aorta Endothelium

Pig aortas were collected at a slaughterhouse, kept on ice during transport, opened along the length and put between two 1.5 cm thick perspex blocks. 10 mm diameter holes had been drilled into the block positioned above the aorta facing the luminal side. Thus, 10 mm diameter wells with aorta endothelium in the bottom were achieved. A solution containing 440,000 cpm $^{125}$I-EC-SOD (labelled as described in Example 10) and a large excess of unlabelled EC-SOD fraction C (121 µg/ml) was prepared. The solvent was Eagle's minimal essential medium dium buffered at pH 7.4 with HEPES and containing 0.5 µg/ml bovine serum albumin. 150 µl of the solution were put in each of three wells and incubated with shaking for 2.5 hours at room temperature. The solution was then sucked off. The wells were then washed twice with 500 µl of solvent (2 minutes with shaking) and then twice with 500 µl of solvent containing 15 IU of heparin (5 minutes with shaking). The radioactivity in the solutions (mean of three wells, % of added activity) was 80.4% (incubated initial solution), 2.1%, 0.6% (wash solutions), 6.5%, 2.2% (wash with heparin). The SOD enzyme activity was determined in solutions from one well and was found to be 84.2% (82.7%) in the incubated initial solution removed and 7.1% (7.0%) in the first heparin wash (corresponding data for radioactivity in brackets). Thus, there was a very good correspondence between SOD enzyme activity and the radioactivity determined. The data show that about 20% of added EC-SOD were bound by the aorta endothelium, and that EC-SOD activity could be released by the addition of heparin.

EXAMPLE 12

Binding of Native and Recombinant EC-SOD to Lectins

Concanavalin Al, lentil lectin and wheat germ lectin immobilized on Sepharose® was obtained from Pharmacia AB, Uppsala, Sweden. 2 ml of each gel were packed in chromatography columns. 50 mM sodium phosphate (pH 7.4)+0.25M NaCl was used as eluant. 200 units (1.7 µg) native umbilical cord EC-SOD or recombinant EC-SOD dissolved in 0.5 ml elution buffer were applied to the lectin columns. 3.5 ml elution buffer was then applied. The columns were washed with 10 ml elution buffer. Bound EC-SOD was then eluted with 14 ml 0.5M α-methylmannoside (ConA Sepharose® and lentil lectin-Sepharose®) or 0.5M N-acetylglucoseamine (wheat germ lectin-Sepharose®). SOD activity was determined on fluid eluting from the columns.

98% of the native EC-SOD and 97% of recombinant EC-SOD bound to the concanavalin A-Sepharose®. 99% of the native EC-SOD, 96% of the recombinant EC-SOD bound to lentil lectin Sepharose®. 61% of the native EC-SOD and 95% of the recombinant EC-SOD bound to wheat germ lectin Sepharose®.

The affinity for concanavalin A and lentil lectin shows that both native and recombinant EC-SOD contain glucosyl and mannosyl residues in their carbohydrate moieties. Affinity for wheat germ lectin indicates the presence of N-acetylglucoseaminyl residues. The heterogeneity of native EC-SOD with regard to binding to wheat germ lectin is probably explained by partial degradation of the carbohydrate part of the enzyme when present within the umbilical cord or within the umbilical cord homogenate during isolation. There is less risk that the recombinant enzyme is exposed to degrading enzymes. To conclude, as deduced from the results of these studies with lectin, the carbohydrate parts of native and recombinant EC-SOD are similar.

EXAMPLE 13

Analysis of Native Umbilical Cord EC-SOD and Recombinant EC-SOD on heparin-Sepharose®

About 500 units (4.4 µg) native EC-SOD C and recombinant EC-SOD were chromatographed on heparin-Sepharose® as described in Example 9. Both enzymes were found to elute at 0.52M in the NaCl gradient. Thus, native and recombinant EC-SOD behaved identically, and the result establishes that the recombinant EC-SOD is of the C-type.

EXAMPLE 14

Content of Copper and Zinc in the EC-SOD Molecule

The content of Cu and Zn in native umbilical cord EC-SOD and of recombinant EC-SOD was determined by means of atomic absorption spectrometry in a graphite furnace in a Perkin-Elmer Zeeman 303+HGA apparatus. The amount of EC-SOD protein and Cu and Zn in the preparations were compared. One mole of native EC-SOD (tetramer) was found to contain 3.97 moles of Cu and 4.50 moles of Zn. The recombinant EC-SOD contained 3.98 moles of Cu and 4.45 moles of Zn per mole enzyme. The two preparations thus contain equal amounts of Cu and Zn. The results confirm the previous finding of 4 moles of Cu per mole of EC-SOD (Marklund, *Proc. Natl. Acad. Sci. USA* 79, 1982, pp. 7634–7638). About four Zn atoms were also found in that investigation, but the presence of zinc in the enzyme could not be established with certainty due to the scarcity of material and the possibility of Zn contamination. The present results now establish that the EC-SOD molecule contains four Zn atoms.

EXAMPLE 15

Preparation of Monoclonal Antibodies Against Human EC-SOD

Mice were injected with EC-SOD C prepared from umbilical cord (Example 4–6). After a few months the mice were injected with EC-SOD on three consecutive days. On the fourth day, the spleens were removed and disintegrated. Spleen cells were fused with a mouse myeloma cell-line according to standard techniques (St. Groth and Scheidegger, *J. Immunol. Methods* 35, 1980, pp. 1–21). Clones producing anti-EC-SOD were identified by means of an ELISA technique (Pouillard and Hoffman, *Methods in Enzymology*, 92, 1983, pp. 168) and further subcloned. Finally, two clones, "14.B7" and "6.H6" were selected for antibody preparation on a larger scale by means of culture in the abdominal cavity of mice. Antibodies were then isolated from the ascites fluid by adsorption on and desorption from Protein A-Sepharose® as recommended by the manufacturer (Pharmacia, Uppsala, Sweden). The elution from the column was performed with 0.1M glycine-HCl pH 3.0. Immediately after elution, the pooled IgG were titrated to pH 7.0 and then dialyzed against 50 mM Tris-HCl pH 8.0+0.15M NaCl+ 0.02% NaN$_3$.

EXAMPLE 16

Immobilization of Monoclonal anti-EC-SOD on CNB3-activated Sepharose®

Since the "6.H6" monoclonal antibody was found to bind n-EC-SOD very strongly Kd<·10$^{12}$M), the "14B7" antibody (Kd~10$^6$M) was selected for EC-SOD purification purposes. Prior to the coupling to CNBr activated Sepharose, the azide in the IgG-solution (cf. Example 15) had to be removed and the buffer had to be changed to a "coupling buffer" (=0.1M Na carbonate pH 8.3+0.5M NaCl). This was performed with a PD10 column by the procedure recommended by the manufacturer (Pharmacia, Uppsala, Sweden). The CNBr-activated Sepharose® was swollen and prepared as recommended by the manufacturer (Pharmacia, Uppsala, Sweden). The CNBr-activated Sepharose® was then added to the IgG-solution (in coupling buffer) in an amount predicted to produce a coupling density of about 2 mg of IgG per ml of gel. The mixture was incubated at room temperature for about 2 hours on a "shaker". The buffer was then removed from the gel and analyzed for remaining protein. Over 97% coupling was achieved. Remaining active groups on the IgG-coupled gel were then blocked by incubation with 1M ethanolamine at pH 9.3 in 2 hours at room temperature. Excess of ethanolamine and adsorbed protein was finally washed away with alternately "coupling buffer" (see above) and 0.1M Na-acetate, pH 4.0+0.5M NaCl, four to five times. The gel was stored in 50 mM potassium phosphate, pH 7.4+0.5M NaCl+0.02% NaN$_3^-$. The maximum binding capacity of the monoclonal IgG-Sepharose® was determined by incubation for 3 hours with an excess of purified EC-SOD (Example 4–6) and subsequent analysis of remaining EC-SOD activity in the supernatant after centrifugation. The result was compared with the analogous incubation with Sepharose® 4B.

To 1 ml of EC-SOD in "coupling buffer", 10, 50, 100 and 1000 µl of a 50% suspension of the monoclonal anti-EC-SOD-Sepharose® were added. A parallel incubation in the same buffer of a 80% suspension of Sepharose® HB was performed. The solutions were incubated at room temperature in 3 hours. After centrifugation the remaining EC-SOD activities in the supernatants were determined. Using the resulting figures it could be calculated that the EC-SOD binding capacity of the gel was about ~6000 units of EC-SOD per ml of 50% gel suspension (=~12000 U/ml of gel). This figure is equal to about 6% of the theoretical maximum binding capacity and is close to what is generally achieved with randomly coupled IgG.

37

EXAMPLE 17

Isolation of Recombinant EC-SOD Staring with Monoclonal anti-EC-SOD Sepharose®

Figure 12:
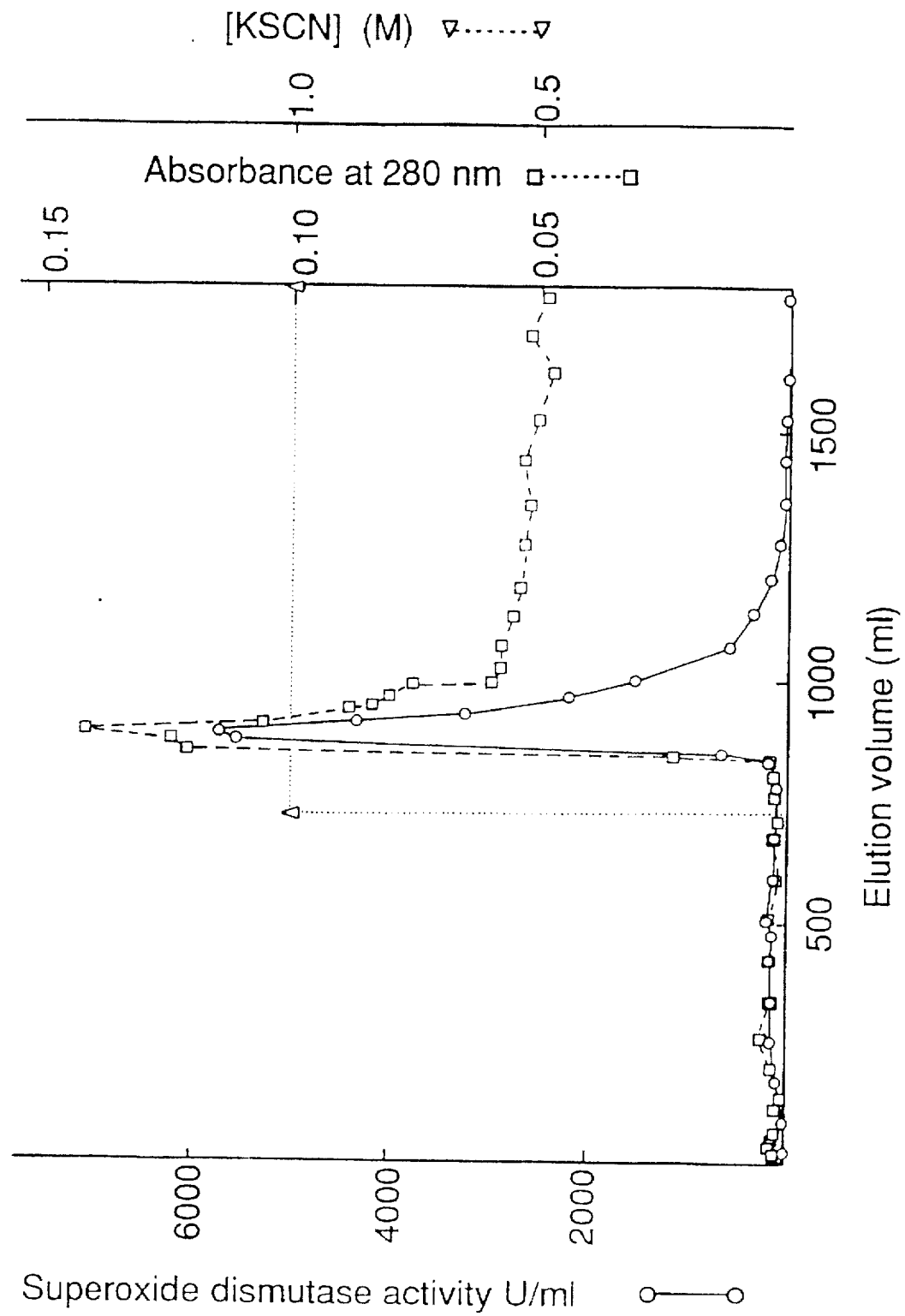
FIG. 12 is a graph showing the elution pattern of recombinant EC-SOD from monoclonal anti-EC-SOD-Sepharose® (cf. Example 17).

The entire purification procedure was performed at +4° C. About 5 liters of medium from cultures of CHO-K1/pPSneo-18 cells, containing about 300 U EC-SOD activity (~2.6 µg) per ml, were centrifuged to remove any cellular debris and precipitates. To bind the EC-SOD in the medium (~1,500,000 units), about 125 ml of monoclonal anti-EC-SOD-Sepharose® was used (Example 16). The IgG-Sepharose was packed in a chromatography column with a diameter of 5 cm and a height of about 6.5 cm. The column was washed with 50 mM sodium phosphate+0.5M NaCl, pH 7.0, prior to "sample application". The culture medium was applied with a rate of 100 ml/h and the absorbance of 280 nm was monitored. Proteins loosely bound to the IgG-Sepharose were eluted with 50 mM sodium phosphate, pH 6.5+0.5M NaCl. The elution continued until a very low $AD_{280}$ was attained. The column was then washed with 650 ml of 50 mM AMP (=1-aminomethylpropanol)-HCl, pH 9.0 and the EC-SOD was eluted with ~1 liter of 50 mM AMP-HCl, pH 9.0+1M KSCN. The elution rate was 100 ml/h. EC-SOD-activity and absorbance at 280 nm were analyzed and plotted versus elution volume (FIG. 12). Remaining absorbance at 280 nm after the protein peak originates from the KSCN. The EC-SOD activity peak was then pooled. To reduce the ionic strength and to optimize the binding of the enzyme for the ion exchange gel, in the following step, the pool was diluted with about 14 volumes of distilled water and finally titrated to pH 8.5 with 2M AMP. The recovery in the IgG-affinity step was 60%.

Figure 13:
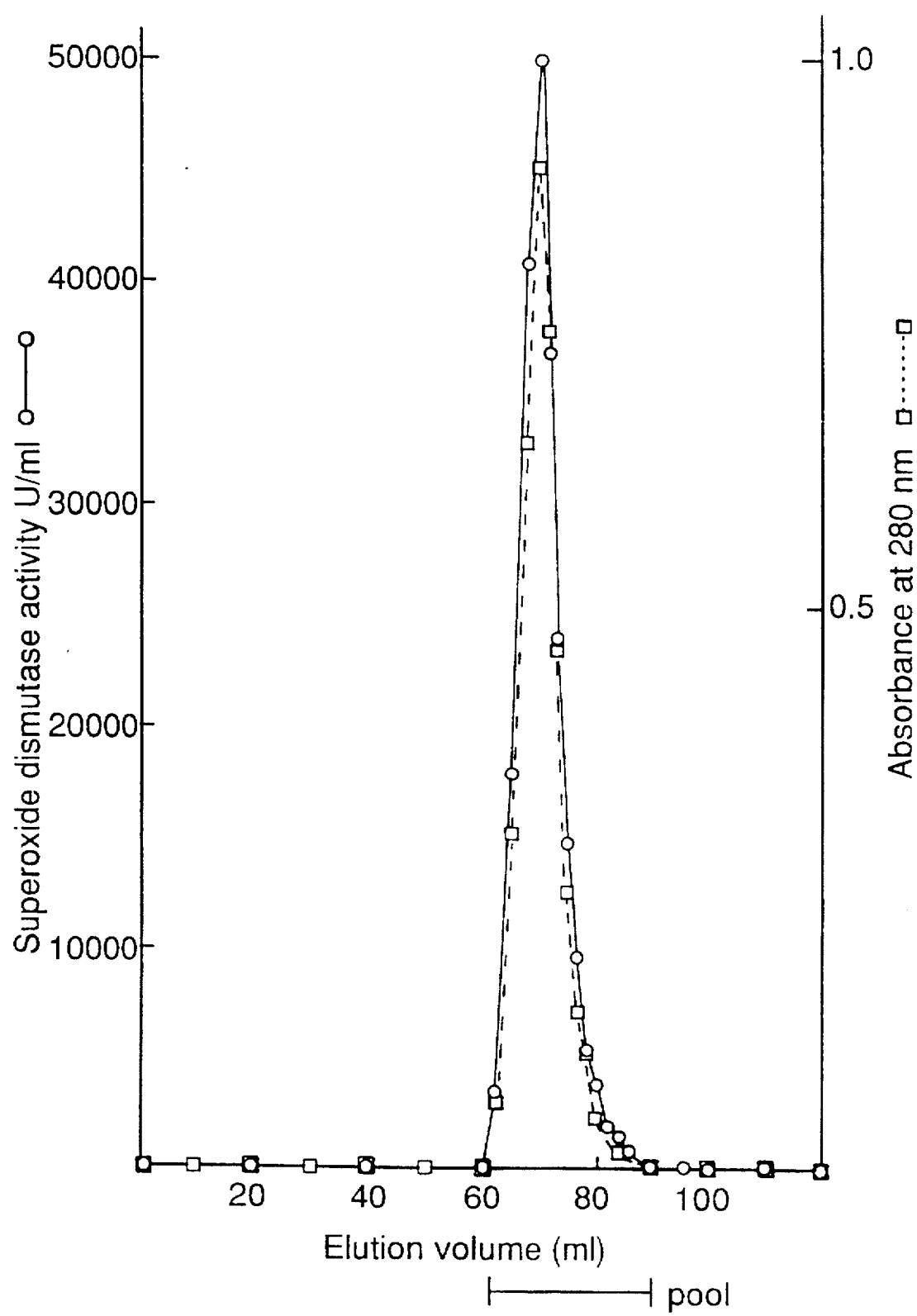
FIG. 13 is a graph showing the elution pattern of recombinant EC-SOD from DEAE-Sephacel® (cf. Example 17).

About 10 ml of DEAE-Sephacel® was washed with 50 mM sodium phosphate, pH 6.5 and packed in a chromatography column with a diameter of 5 cm to a height of about 0.5 cm. The diluted EC-SOD pool from the IgG-column was allowed to adsorb to the DEAE-Sephacel® by pumping the pool through the column with a rate of 60 ml/h. The column was then washed with 50 mM sodium phosphate, pH 8.5 until the absorbance at 280 nm was close to zero. The enzyme was eluted with 50 mM sodium phosphate, pH 8.5+0.25M NaCl. The absorbance at 280 nm and the EC-SOD activity was analyzed and plotted versus elution volume (FIG. 13). The peak fractions were pooled, dialyzed against 50 mM sodium phosphate pH 6.5 and concentrated to about 6 ml. The recovery in this step was about 100%.

The EC-SOD was finally purified by adsorption/desorption on heparin-Sepharose®. 12 ml of heparin-Sepharose® were prepared as recommended by the manufacturer (Pharmacia, Uppsala, Sweden) and washed with 50 mM sodium phosphate pH 6.5+1M NaCl and then with 50 mM sodium phosphate pH 6.5. The heparin-Sepharose® gel was packed in a chromatography column with a diameter of 2.5 cm (height about 2.5 cm). The concentrated and dialyzed pool from the DEAE Sephacel® column (6 ml with an EC-SOD-activity of about 185,000 U/ml, was applied on the column with an elution rate of 10 ml/h. The absorbance at 280 nm was monitored. The elution was started with 50 mM sodium phosphate pH 6.5 and en elution rate of 20 ml/h. When the absorbance at 280 nm approached the baseline, the EC-SOD was eluted with a NaCl gradient from 0M to 1M NaCl. The gradient volume was 270 ml. To protect the EC-SOD from the high NaCl concentration, the fractions were diluted (from the start of the gradient) with distilled water. A T-pipe was inserted into the plastic tube from the eluting end of the column, and distilled water was pumped into the eluting fluid at twice the column elution rate.

38

Figure 14:
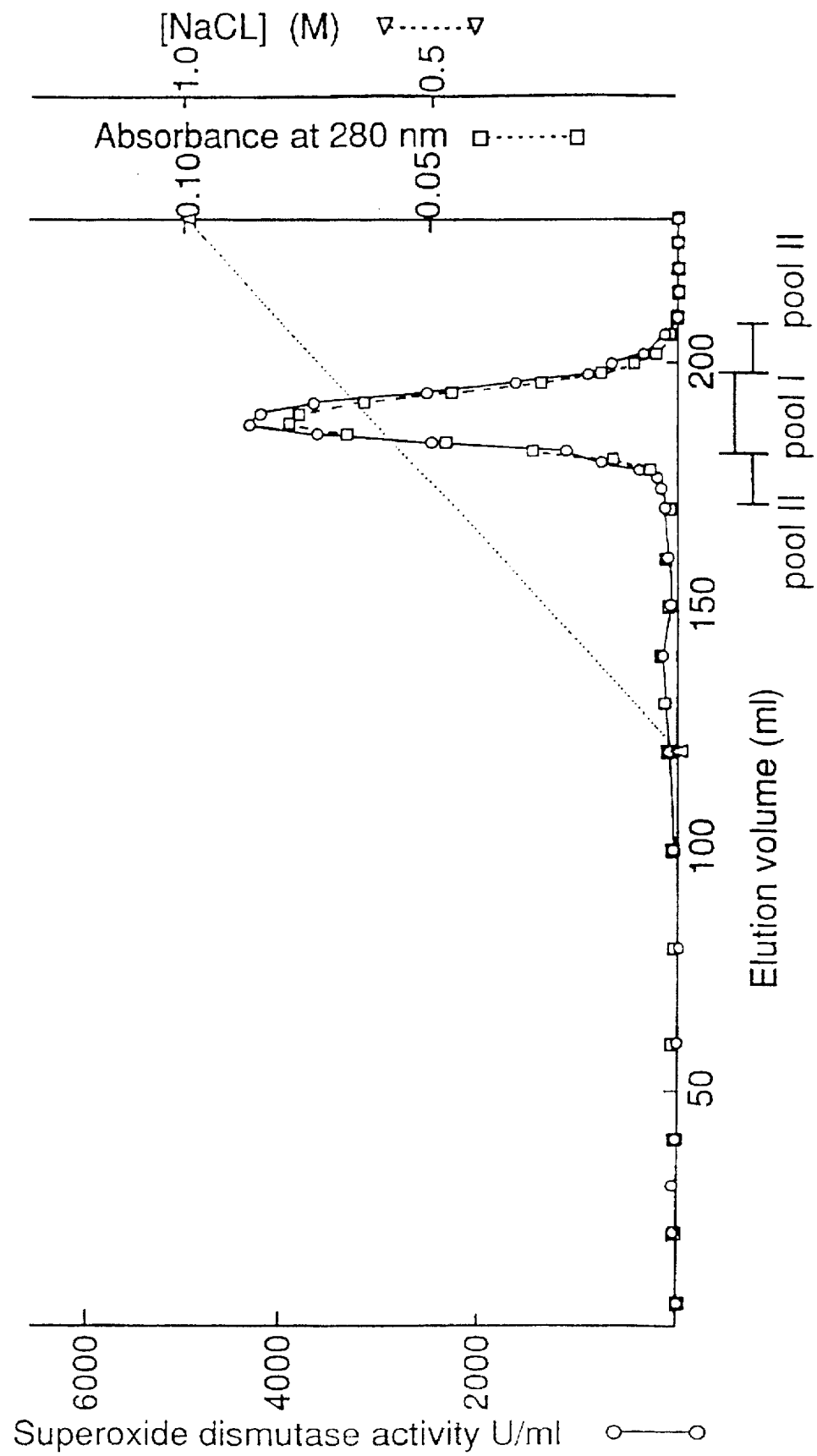
FIG. 14 is a graph showing the elution pattern of recombinant EC-SOD from heparin-Sepharose® (cf. Example 17).

The EC-SOD-activity eluted in one peak (FIG. 14) at about the same NaCl concentration as the the C peak in Example 6. The center of the peak was pooled (Pool I). The specific activity of Pool I (U/ml divided by $AD_{280}$) was 88,400. The specific activity of native EC-SOD prepared from umbilical cord homogenate (cf. Example 1) by the same procedure was 88,200. These figures are therefore almost identical and somewhat higher than previously published (Marklund, *Proc. Natl. Acad. Sci. USA* 79, 1982, pp. 7634–7638). These two preparations were analyzed in examples 12–14 and 18–20. The sides of the peak were also pooled (Pool II). The pools were concentrated and dialyzed against 50 mM sodium phosphate, pH 6.6. The yield of EC-SOD was about 60% in the heparin-Sepharose® step. The pools contained 60,000 U (about 5.3 mg) in all which is 40% of the original activity in the CHO-K1/pPS3neo-18 culture medium.

EXAMPLE 18

Determination of Molecular Size of Native EC-SOD and Recombinant EC-SOD by Means of Gel Chromatography The molecular weight of the native enzyme from umbilical cord and the recombinant enzyme was estimated by means of gel filtration on a Sephacryl S-300® column. The column (1.6 cm in diameter, length 96 cm) was eluted with 10 mM potassium phosphate, pH 7.4+0.15M NaCl as eluent. The column was calibrated with ferritin (440,000), IgG (150,000), bovine serum albumin (67,000), ovalbumin (43,000), chymotrypsinogen (25,000), and ribonuclease (13,700) (molecular weights in parenthesis).

Native and recombinant EC-SOD eluted from the column at positions corresponding to molecular weights of 136,000 and 151,000 respectively. The recombinant EC-SOD thus appeared to be slightly larger. Part of the difference may be due to the partial degradation of the subunits of the native enzyme as seen in the SDS-PAGE experiments below (Example 19). The heterogenicity of native EC-SOD upon chromatography on wheat germ lectin (Example 12) also points to partial degradation of the carbohydrate part of the enzymes.

EXAMPLE 19

Analysis of Native Umbilical Cord EC-SOD and Recombinant EC-SOD by Means of Electrophoresis in Gradient Polyocrylomide Gels in the Presence of Sodium Dodecyl Sulphate The molecular weight of the subunits of native- and recombinant EC-SOD was compared by electrophoresis in gradient gels (10–15% in the presence of SDS.

Figure 15:
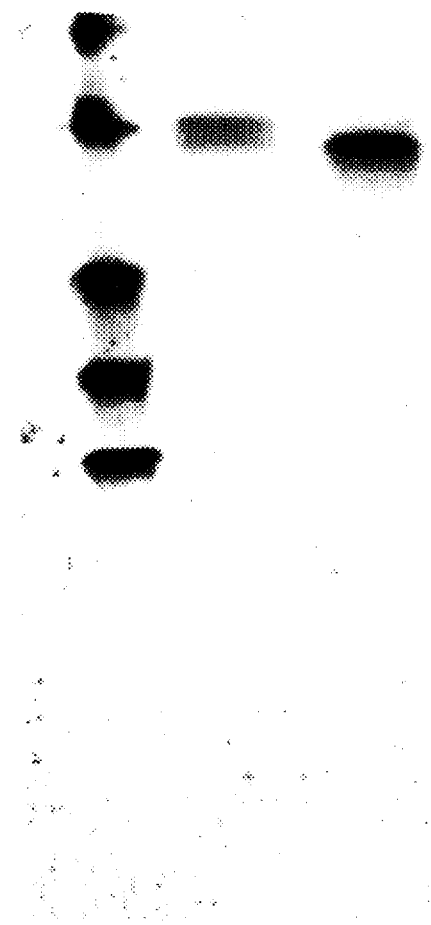
FIG. 15 shows the electrophoresis of native and recombinant EC-SOD on gradient polyacrylamide gels in the presence of sodium dodecyl sulphate (cf. Example 19).

Approximately 25 µg of each enzyme (n-EC-SOD and r-EC-SOD) were freeze-dried and then dissolved in 50 µg of a sample mixture containing 5% sucrose, 5 mM EDTA, 5% 2-mercaptoethanol and 2% SDS in a buffer composed of 0.4M boric acid and 0.41M Tris, pH 8.64. The samples were boiled for 5 minutes and immediately cooled on ice. About 1 µl (about 0.2 µg) of each sample was applied on a Pharmacia Phast System gradient (10–15%) polyacrylamide gel and then run on a Pharmacia Phast System Instrument as recommended by the manufacturer (Pharmacia, Uppsala, Sweden in Phast System™ Separation Technique File No. 110). The resulting gel was stained with Coomassie brilliant blue, cf. FIG. 15. From left to right the lanes contain recombinant EC-SOD, native umbilical cord EC-SOD and a mixture of molecular weight markers (94,000, 67000, 43,000, 29,000, 20,100 and 14,400). The marker with a mobility similar to the EC-SOD's is 29,000 in molecular weight. No impurities could be detected in the EC-SOD's. Recombinant EC-SOD has one band with a molecular weight of about 32,000. Native EC-SOD shows two bands, the larger with apparently the same molecular weight as recombinant EC-SOD and the smaller with a molecular weight of about 28,000. The relative amounts of the two bands vary from preparation to preparation of native EC-SOD and the heterogeneity is probably due to partial degradation of the enzyme.

EXAMPLE 20

Comparison Between the Amino Acid Composition of Native and Recombinant EC-SOD and the Amino Acid Sequence Deduced from the cDNA Sequence Encoding EC-SOD The amino acid composition of native umbilical cord ECSOD and recombinant EC-SOD is shown in Table II. Tryptophan was not included in the comparison since it cannot be reliably obtained in an amino acid analyser. It appears from the Table that the native and recombinant enzymes are almost identical in composition. The agreement with the figures deduced from the cDNA sequence is also very good. The results indicate that the native and recombinant enzymes are virtually identical and that the amino acid sequence deduced from the cDNA sequence is correct.

TABLE II

Amino acid composition of human EC-SOD

% residues/total residues

| Amino acid | from DNA sequence $^+$Trp | from DNA sequence $^-$Trp | native enzyme $^-$Trp | recombinant enzyme $^-$Trp |
|---|---|---|---|---|
| Phe | 3.2 | 3.2 | 3.3 | 3.2 |
| Leu | 6.3 | 6.5 | 6.8 | 6.7 |
| Ile | 1.8 | 1.8 | 1.6 | 1.4 |
| Met | 0.9 | 0.9 | 1.2 | 0.9 |
| Val | 7.7 | 7.8 | 6.4 | 6.2 |
| Ser | 6.8 | 6.9 | 6.8 | 7.8 |
| Pro | 5.9 | 6.0 | 6.1 | 6.2 |
| Thr | 3.2 | 3.2 | 2.9 | 3.4 |
| Ala | 12.2 | 12.4 | 13.1 | 12.5 |
| Tyr | 1.4 | 1.4 | 1.5 | 1.4 |
| His | 4.1 | 4.1 | 4.2 | 3.9 |
| Gln | 5.0 | 5.1 | — | — |
| Glu | 6.8 | 6.9 | — | — |
| Glx | 11.7 | 12.0 | 11.7 | 12.1 |
| Asn | 3.2 | 3.2 | — | — |
| Asp | 5.9 | 6.0 | — | — |
| Asx | 9.0 | 9.2 | 9.3 | 9.3 |
| Lys | 2.3 | 2.3 | 1.9 | 2.5 |
| Cys | 2.7 | 2.8 | 2.8 | 2.8 |
| Trp | 2.3 | — | — | — |
| Arg | 9.0 | 9.2 | 9.8 | 9.4 |
| Gly | 9.9 | 10.1 | 10.5 | 10.4 |

We claim:

1. A non-naturally occurring pharmaceutical composition which consists essentially of a therapeutically or prophylactically effective amount of EC-SOD together with a pharmaceutically acceptable excipient, diluent or vehicle.

2. A pharmaceutical composition according to claim 1 in which the EC-SOD has a strong affinity for heparin.

3. A pharmaceutical composition according to claim 1 which further comprises a strongly negatively charged compound capable of inducing the release of EC-SOD from cell surfaces.

4. The composition of claim 1 which further comprises an antioxidant cooperating with EC-SOD to reduce the toxic effects of superoxide radicals.

5. The composition of claim 4 in which the antioxidant is catalase.

6. The composition of claim 1 wherein the effective amount is of EC-SOD type C.

7. The composition of claim 1 wherein the effective amount is an amount effective for the treatment of ischemia.

8. The composition of claim 1 wherein the effective amount is an amount effective for the treatment of an inflammatory disease.

9. The composition of claim 1 wherein the EC-SOD is of placental or umbilical cord origin.

* * * * *